(12) United States Patent
Thenuwara et al.

(10) Patent No.: US 8,753,353 B2
(45) Date of Patent: *Jun. 17, 2014

(54) TOOLS, SYSTEMS, AND METHODS FOR INSERTING AN ELECTRODE ARRAY PORTION OF A LEAD INTO A BODILY ORIFICE

(75) Inventors: Chuladatta Thenuwara, Castaic, CA (US); Rosa Gallegos, Sylmar, CA (US); Timothy Beerling, Los Angeles, CA (US)

(73) Assignee: Advanced Bionics AG, Zug (CH)

( * ) Notice: Subject to any disclaimer, the term of this patent is extended or adjusted under 35 U.S.C. 154(b) by 822 days.

This patent is subject to a terminal disclaimer.

(21) Appl. No.: 12/824,120

(22) Filed: Jun. 25, 2010

(65) Prior Publication Data

US 2011/0319909 A1 Dec. 29, 2011

(51) Int. Cl.
*A61B 19/00* (2006.01)
(52) U.S. Cl.
USPC ........................................... 606/129
(58) Field of Classification Search
USPC ................... 606/129; 607/136, 137, 56, 116; 600/379
See application file for complete search history.

(56) References Cited

U.S. PATENT DOCUMENTS

| | | | |
|---|---|---|---|
| 3,530,860 A | 9/1970 | Majoros | |
| 3,973,560 A | 8/1976 | Emmett | |
| 4,180,080 A | 12/1979 | Murphy | |
| 4,280,510 A | 7/1981 | O'Neill | |
| 4,488,561 A | 12/1984 | Doring | |
| 4,532,930 A | 8/1985 | Crosby et al. | |
| 4,646,755 A | 3/1987 | Kane | |
| 4,665,918 A | 5/1987 | Garza et al. | |
| 4,787,884 A | 11/1988 | Goldberg | |
| 4,819,647 A | 4/1989 | Byers et al. | |
| 4,865,037 A | 9/1989 | Chin et al. | |
| 4,898,183 A | 2/1990 | Kuzma | |

(Continued)

FOREIGN PATENT DOCUMENTS

| | | |
|---|---|---|
| EP | 0109304 | 5/1984 |
| EP | 0328597 | 8/1989 |

(Continued)

OTHER PUBLICATIONS

International Search Report and Written Opinion received in International Application No. PCT/US2011/041576, dated Sep. 19, 2011.

(Continued)

*Primary Examiner* — Katherine Dowe
*Assistant Examiner* — Erin Colello
(74) *Attorney, Agent, or Firm* — ALG Intellectual Property, LLC

(57) ABSTRACT

Exemplary insertion tools, systems, and methods for inserting an electrode array portion of a lead into a bodily orifice are described herein. An exemplary insertion tool includes a handle assembly, a slider assembly, a retractor assembly disposed at least partially within the handle assembly, and a rocker lever. The retractor assembly may include a stiffening member configured to be inserted into the electrode array portion and a spring-loaded retractor member coupled at a proximal end of the stiffening member. The spring-loaded retractor member may be configured to move from a distal position to a proximal position to at least partially retract the stiffening member from the electrode array portion. The rocker lever may be configured to selectively retain the spring-loaded retractor member in the distal position. Corresponding tools, systems, and methods are also described.

19 Claims, 26 Drawing Sheets

(56) References Cited

U.S. PATENT DOCUMENTS

| | | | |
|---|---|---|---|
| 4,994,069 A | 2/1991 | Ritchart et al. | |
| 5,046,497 A | 9/1991 | Millar | |
| 5,110,529 A | 5/1992 | Arima | |
| 5,159,861 A | 11/1992 | Anderson | |
| 5,312,415 A | 5/1994 | Palermo | |
| 5,314,464 A * | 5/1994 | KenKnight et al. | 607/132 |
| 5,443,493 A | 8/1995 | Byers et al. | |
| 5,545,200 A | 8/1996 | West et al. | |
| 5,545,219 A | 8/1996 | Kuzma | |
| 5,558,673 A | 9/1996 | Edwards et al. | |
| 5,579,780 A * | 12/1996 | Zadini et al. | 600/585 |
| 5,645,585 A | 7/1997 | Kuzma | |
| 5,667,514 A | 9/1997 | Heller | |
| 5,749,371 A * | 5/1998 | Zadini et al. | 600/585 |
| 5,810,852 A | 9/1998 | Greenberg et al. | |
| 5,814,062 A | 9/1998 | Sepetka et al. | |
| 5,902,331 A | 5/1999 | Bonner et al. | |
| 5,906,619 A | 5/1999 | Olson et al. | |
| 5,999,859 A | 12/1999 | Jolly | |
| 6,070,105 A | 5/2000 | Kuzma | |
| 6,071,282 A | 6/2000 | Fleischman | |
| 6,078,841 A * | 6/2000 | Kuzma | 607/137 |
| 6,093,197 A | 7/2000 | Bakula et al. | |
| 6,119,044 A | 9/2000 | Kuzma | |
| 6,125,302 A * | 9/2000 | Kuzma | 607/137 |
| 6,129,753 A | 10/2000 | Kuzma | |
| 6,149,657 A * | 11/2000 | Kuzma | 606/129 |
| 6,163,729 A * | 12/2000 | Kuzma | 607/137 |
| 6,195,586 B1 * | 2/2001 | Kuzma | 607/137 |
| 6,208,882 B1 | 3/2001 | Lenarz et al. | |
| 6,219,580 B1 | 4/2001 | Faltys et al. | |
| 6,272,382 B1 | 8/2001 | Faltys et al. | |
| 6,293,945 B1 * | 9/2001 | Parins et al. | 606/45 |
| 6,304,785 B1 * | 10/2001 | McCreery et al. | 607/116 |
| 6,308,101 B1 | 10/2001 | Faltys et al. | |
| 6,312,429 B1 * | 11/2001 | Burbank et al. | 606/47 |
| 6,321,125 B1 | 11/2001 | Kuzma | |
| 6,421,569 B1 | 7/2002 | Treaba et al. | |
| 6,500,130 B2 | 12/2002 | Kinsella et al. | |
| 6,547,762 B1 * | 4/2003 | Botich et al. | 604/110 |
| 6,582,441 B1 | 6/2003 | He et al. | |
| 6,604,283 B1 | 8/2003 | Kuzma | |
| 6,746,412 B1 | 6/2004 | Hill et al. | |
| 6,858,034 B1 | 2/2005 | Hijlkema et al. | |
| 6,866,669 B2 | 3/2005 | Buzzard | |
| 6,936,065 B2 | 8/2005 | Khan et al. | |
| 6,939,352 B2 | 9/2005 | Buzzard | |
| 6,968,238 B1 * | 11/2005 | Kuzma | 607/137 |
| 7,050,858 B1 * | 5/2006 | Kuzma et al. | 607/137 |
| 7,063,708 B2 | 6/2006 | Gibson et al. | |
| 7,269,461 B2 | 9/2007 | Dadd et al. | |
| 7,349,744 B2 * | 3/2008 | Dadd et al. | 607/137 |
| 7,544,197 B2 | 6/2009 | Kelsch et al. | |
| 7,591,268 B2 | 9/2009 | Lowe et al. | |
| 7,753,887 B2 * | 7/2010 | Botich et al. | 604/164.12 |
| 7,792,586 B2 | 9/2010 | Dadd et al. | |
| 7,966,077 B2 * | 6/2011 | Risi | 607/137 |
| 2002/0045927 A1 | 4/2002 | Moore et al. | 607/116 |
| 2002/0143302 A1 * | 10/2002 | Hinchliffe et al. | 604/272 |
| 2002/0147484 A1 | 10/2002 | Dahl | |
| 2003/0045921 A1 | 3/2003 | Dadd et al. | |
| 2003/0093139 A1 | 5/2003 | Gibson et al. | |
| 2003/0171758 A1 * | 9/2003 | Gibson et al. | 606/129 |
| 2004/0122312 A1 * | 6/2004 | Chesbrough et al. | 600/431 |
| 2004/0127968 A1 | 7/2004 | Kuzma et al. | |
| 2004/0193203 A1 * | 9/2004 | Pak et al. | 606/187 |
| 2004/0220651 A1 | 11/2004 | Kuzma et al. | |
| 2004/0243177 A1 | 12/2004 | Svehla et al. | |
| 2004/0260371 A1 | 12/2004 | Greenland et al. | |
| 2005/0004644 A1 | 1/2005 | Kelsch et al. | |
| 2005/0075606 A1 | 4/2005 | Botich et al. | |
| 2005/0251237 A1 | 11/2005 | Kuzma et al. | |
| 2006/0058861 A1 * | 3/2006 | Gibson et al. | 607/137 |
| 2006/0155353 A1 | 7/2006 | Heil, Jr. | |
| 2006/0241723 A1 * | 10/2006 | Dadd et al. | 607/57 |
| 2007/0043419 A1 | 2/2007 | Nikolchev et al. | |
| 2007/0111175 A1 * | 5/2007 | Raven et al. | 434/262 |
| 2007/0213812 A1 | 9/2007 | Webler et al. | |
| 2007/0233214 A1 | 10/2007 | Chitre et al. | |
| 2008/0004684 A1 | 1/2008 | Dadd et al. | |
| 2008/0082141 A1 * | 4/2008 | Risi | 607/57 |
| 2008/0109011 A1 | 5/2008 | Thenuwara et al. | |
| 2008/0195146 A1 | 8/2008 | Wardle | |
| 2008/0269740 A1 * | 10/2008 | Bonde et al. | 606/53 |
| 2008/0269763 A1 * | 10/2008 | Bonde et al. | 606/99 |
| 2009/0119920 A1 | 5/2009 | Peschke et al. | |
| 2011/0301681 A1 | 12/2011 | Risi | |

FOREIGN PATENT DOCUMENTS

| | | |
|---|---|---|
| EP | 1233810 | 8/2002 |
| EP | 1341578 | 9/2003 |
| EP | 1370205 | 12/2003 |
| EP | 1370205 B1 * | 12/2003 |
| EP | 1476104 | 11/2004 |
| EP | 2039323 | 3/2009 |
| WO | WO-80/02231 | 10/1980 |
| WO | WO-8900870 | 2/1989 |
| WO | WO-9324058 | 12/1993 |
| WO | WO-95/11710 | 5/1995 |
| WO | WO-9720530 | 6/1997 |
| WO | WO-00/64529 | 11/2000 |
| WO | WO-00/71063 | 11/2000 |
| WO | WO-01/68177 | 9/2001 |
| WO | WO-02/30507 | 4/2002 |
| WO | WO-0230507 | 4/2002 |
| WO | WO-0232498 | 4/2002 |
| WO | WO-02074211 | 9/2002 |
| WO | WO-03/070133 | 8/2003 |
| WO | WO-03070133 | 8/2003 |
| WO | WO-2004/014472 | 2/2004 |
| WO | WO-2004012809 | 2/2004 |
| WO | WO-2005/110529 | 11/2005 |
| WO | WO-2010/045228 A3 | 4/2010 |
| WO | WO-2010/133704 A2 | 11/2010 |
| WO | WO-2011/005993 A1 | 1/2011 |

OTHER PUBLICATIONS

Non-Final Office Action received in U.S. Appl. No. 12/425,868, dated Nov. 25, 2011.

International Search Report and Written Opinion received in International Application No. PCT/US2011/041577, dated Nov. 30, 2011.

Final Office Action received in U.S. Appl. No. 12/425,868, dated Jul. 6, 2012.

Non-Final Office Action received in U.S. Appl. No. 12/824,119, dated Jun. 8, 2012.

International Search Report and Written Opinion received in International Application No. PCT/US2007/083428 dated May 20, 2008.

* cited by examiner

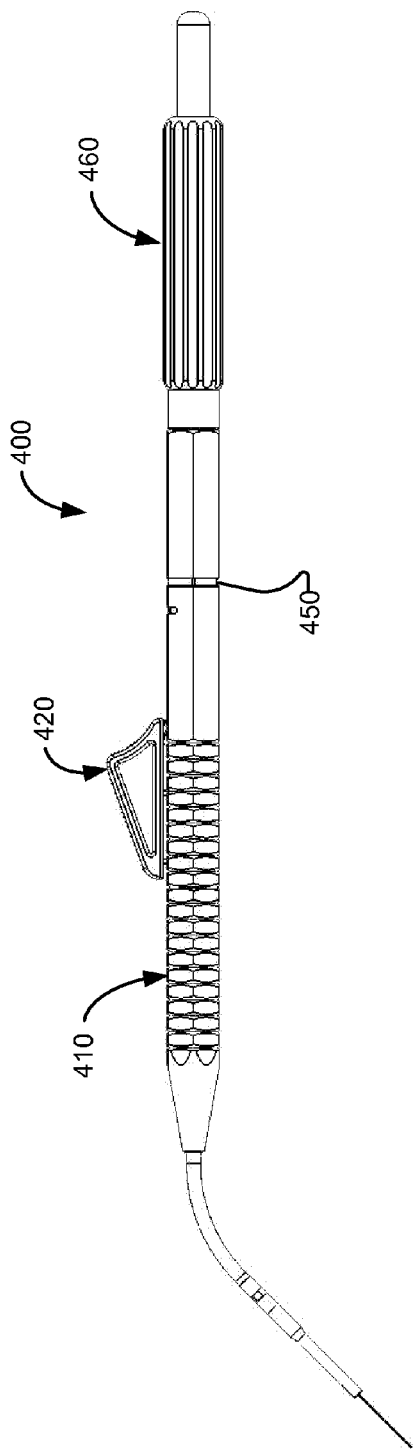
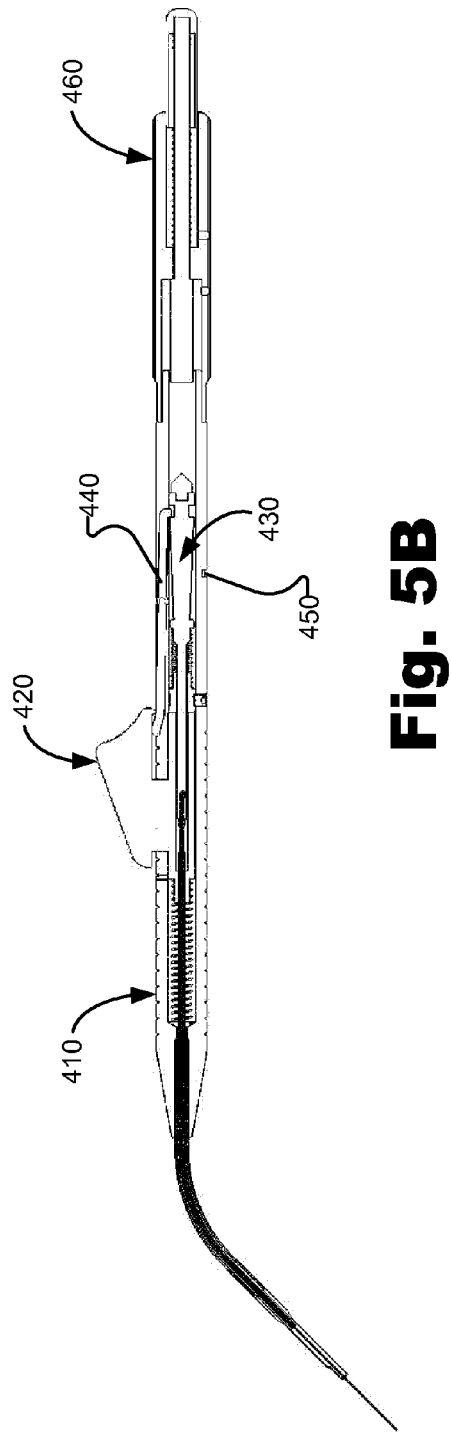
Fig. 5A
Fig. 5B

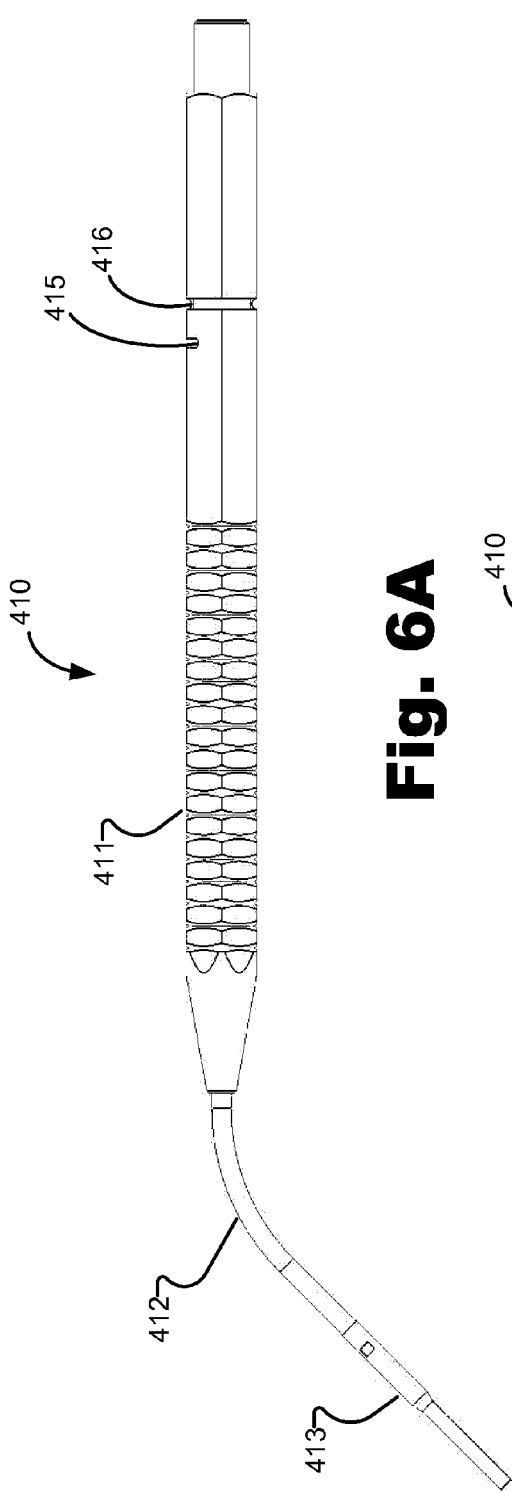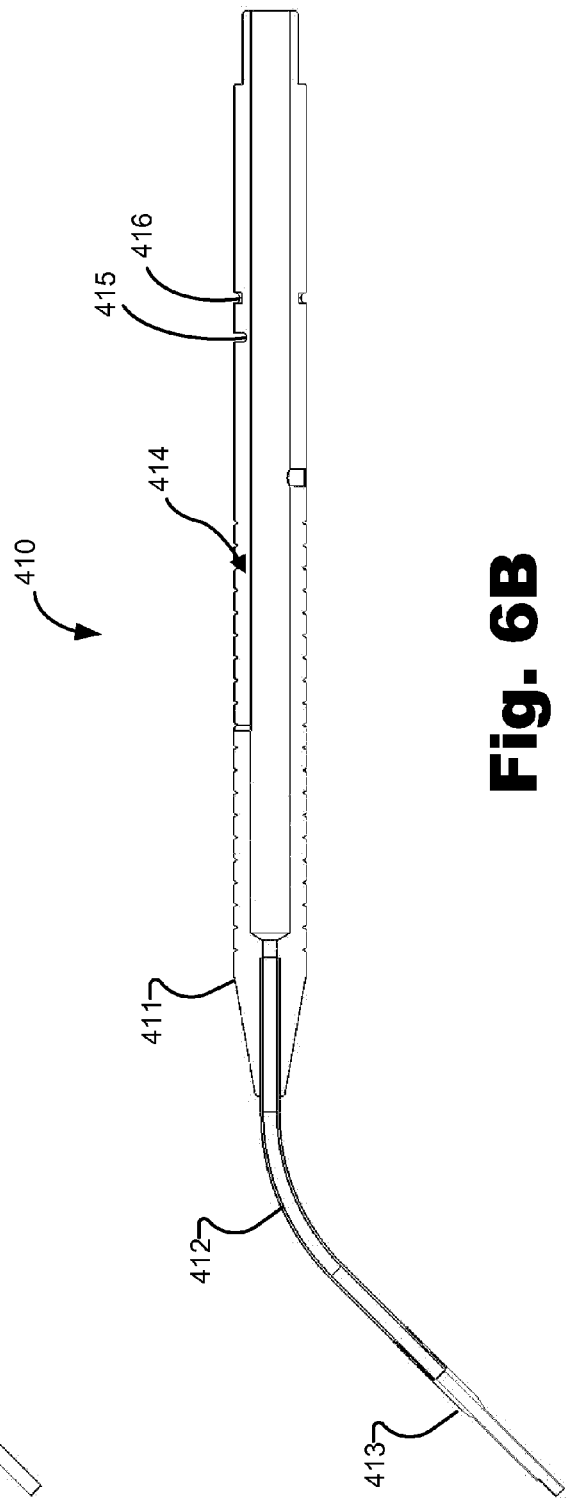

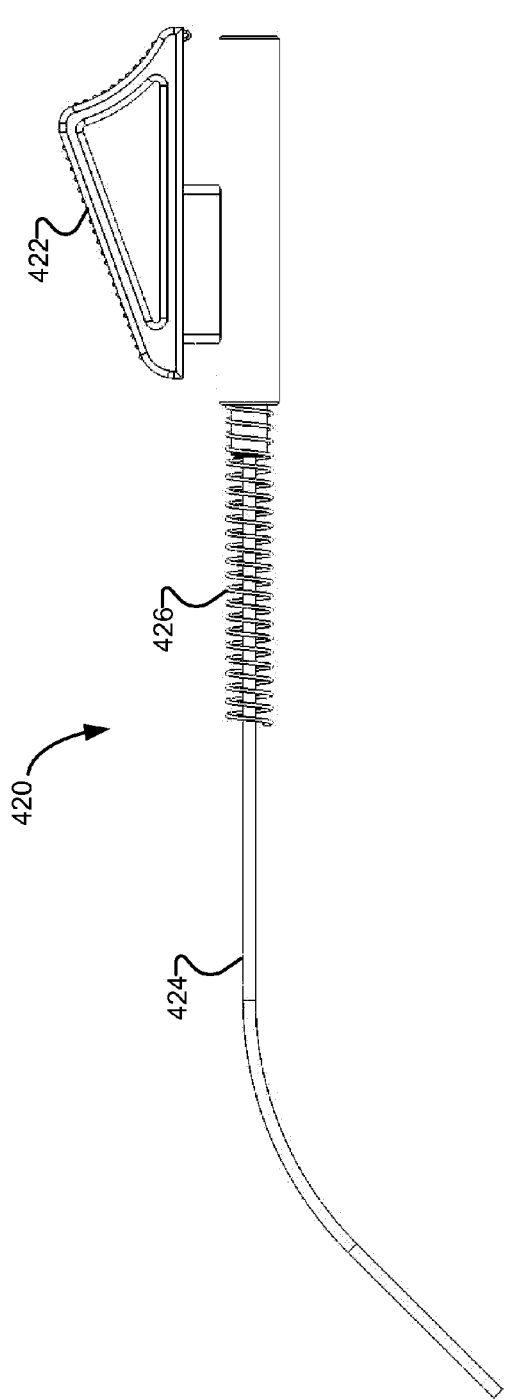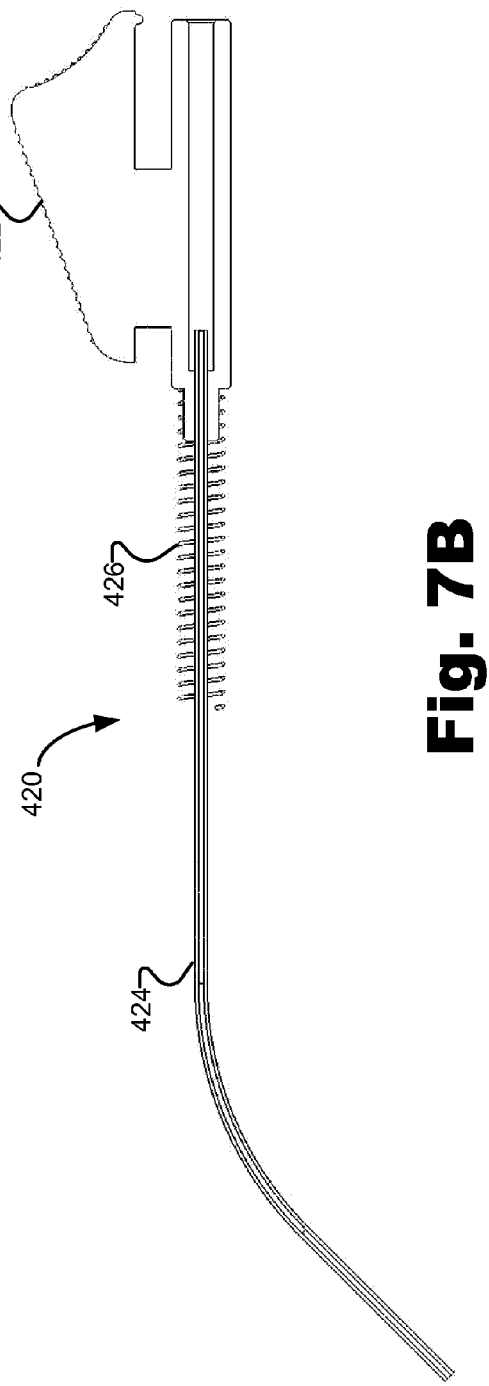

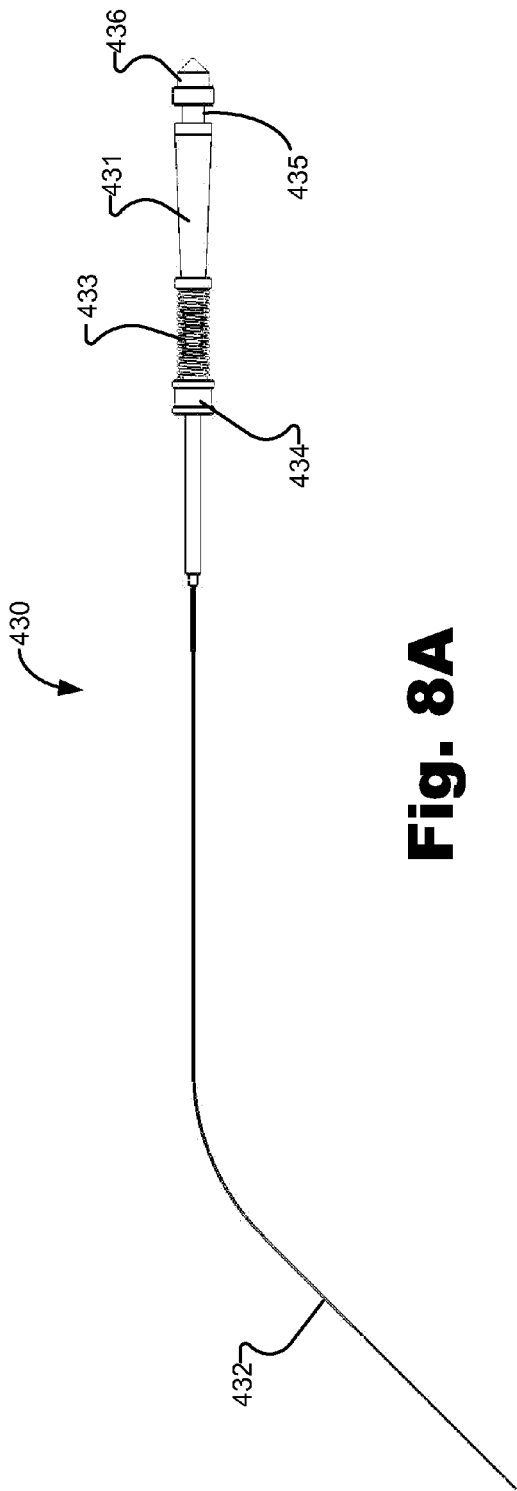
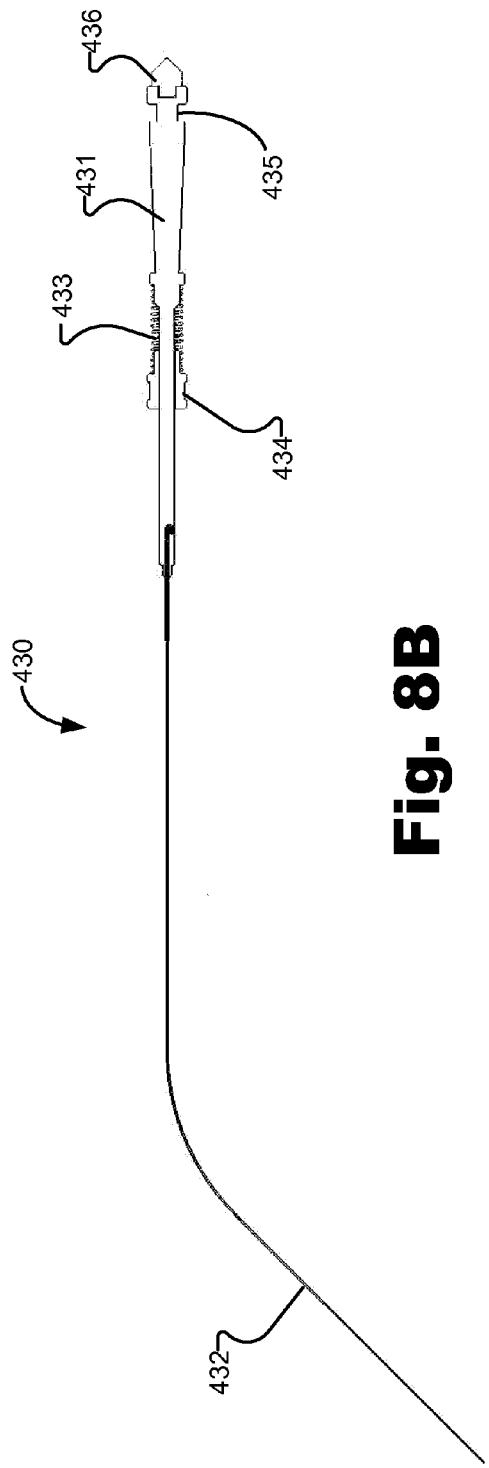
Fig. 8A
Fig. 8B

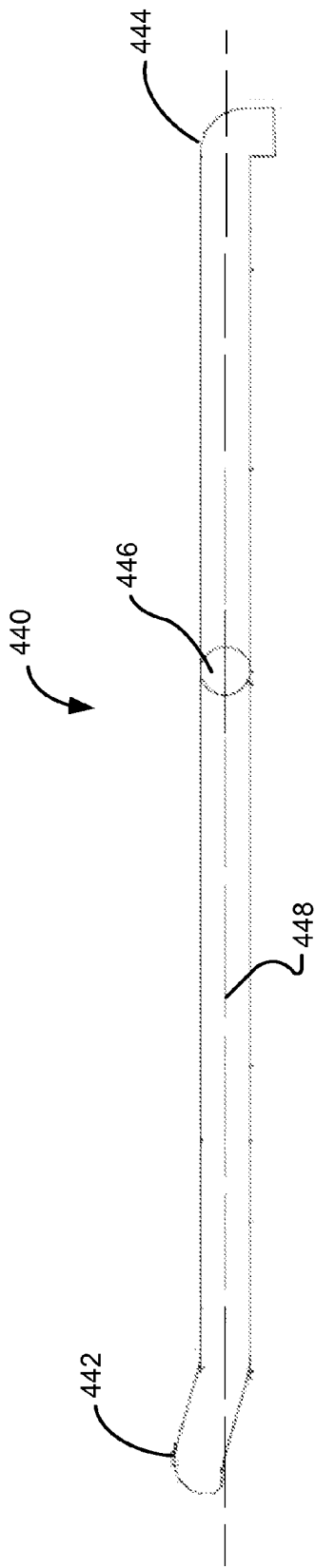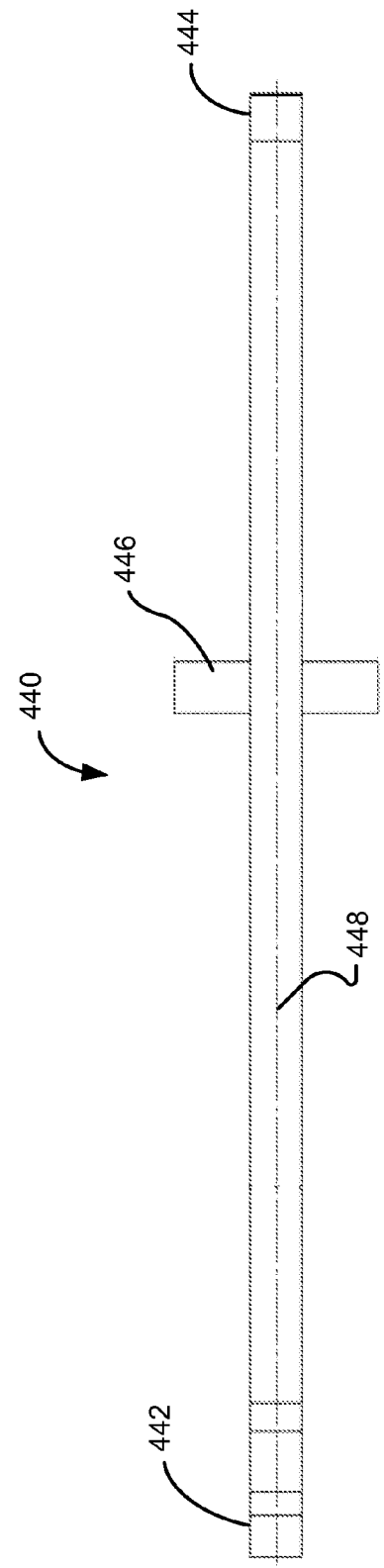

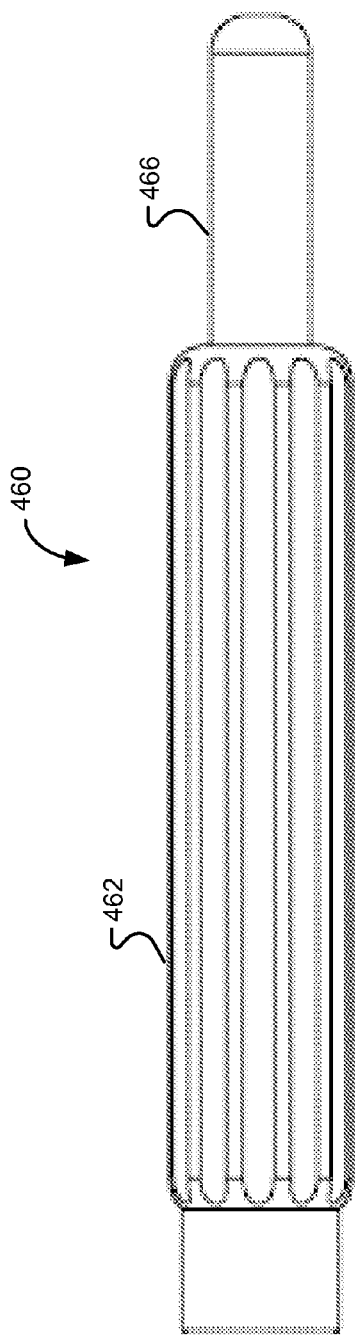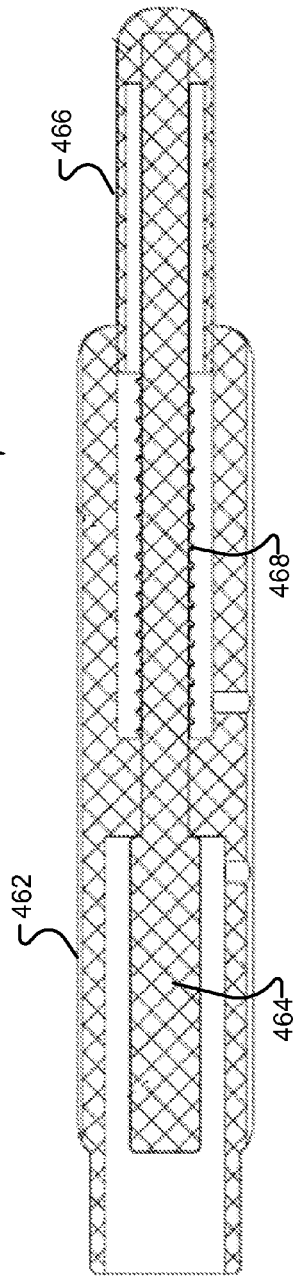
Fig. 11A
Fig. 11B

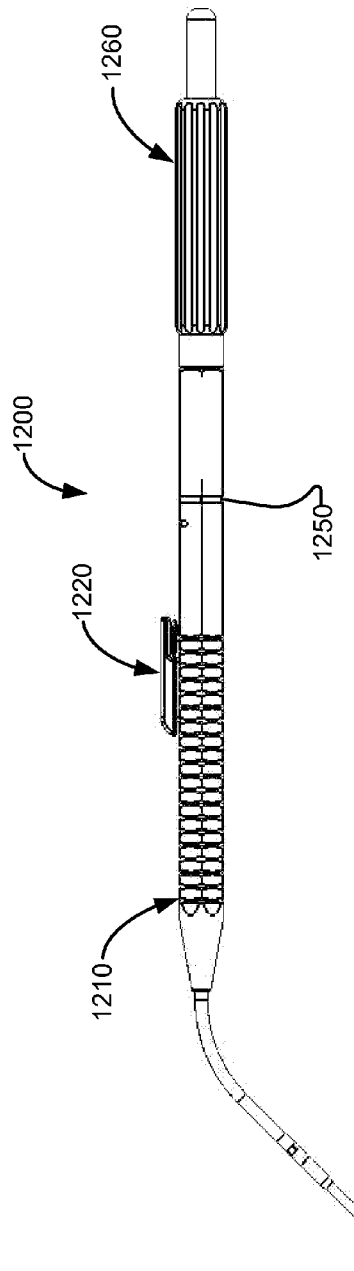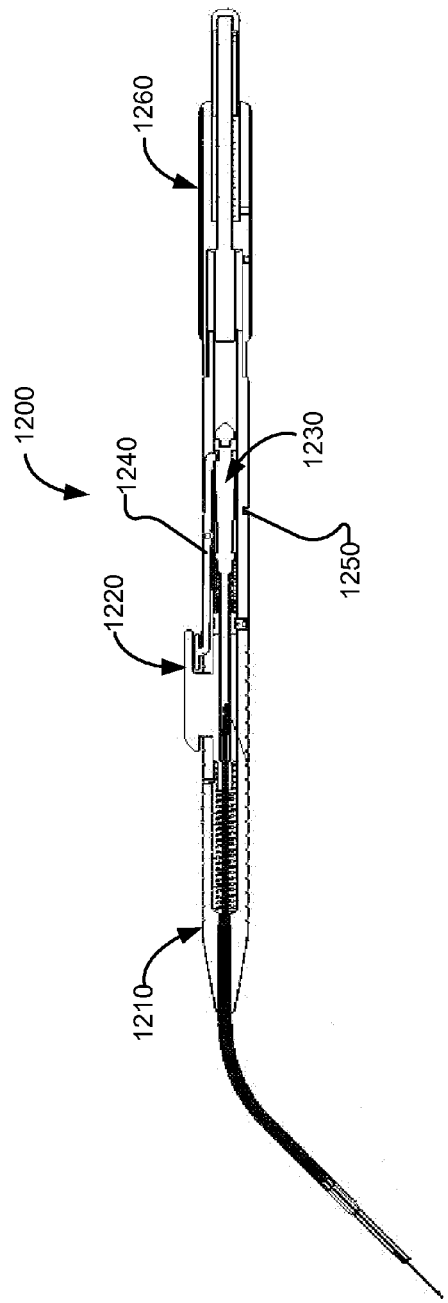

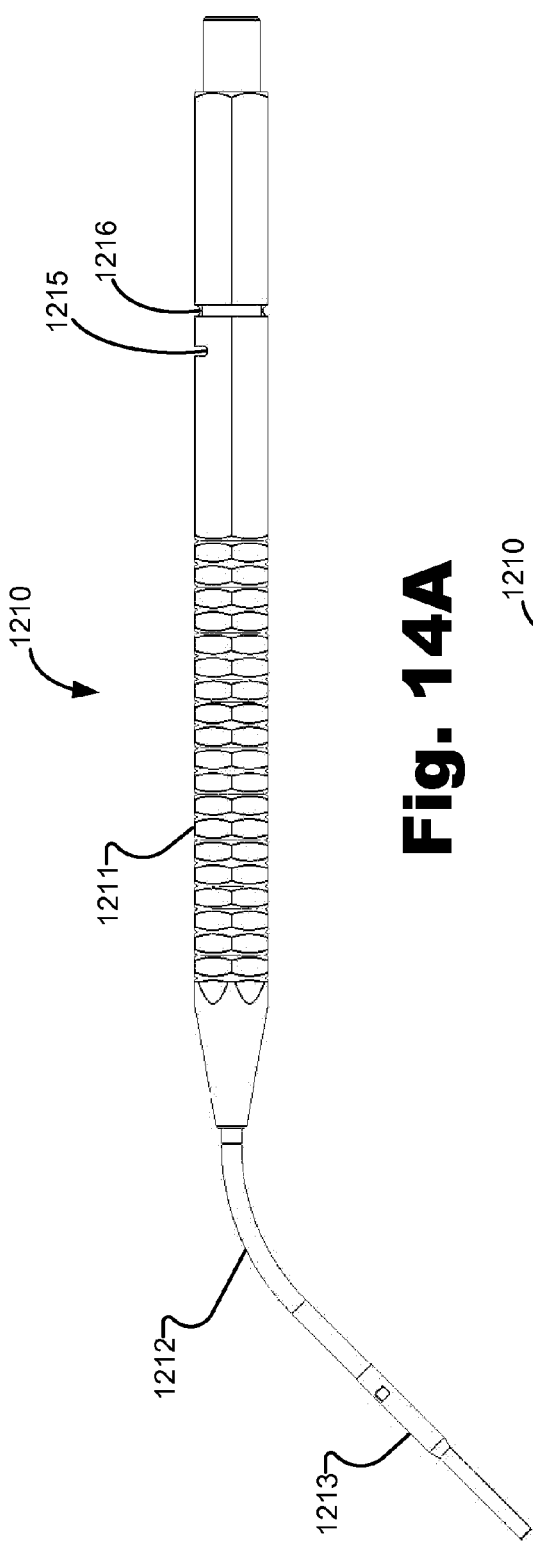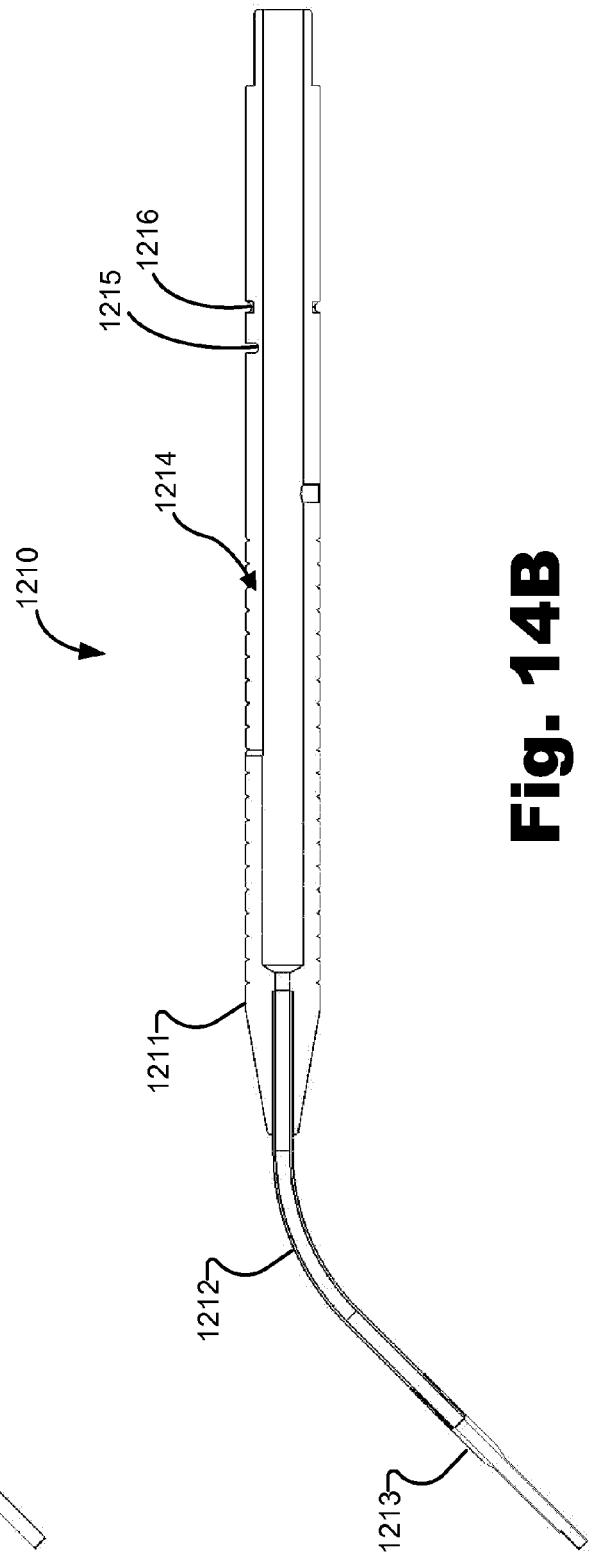

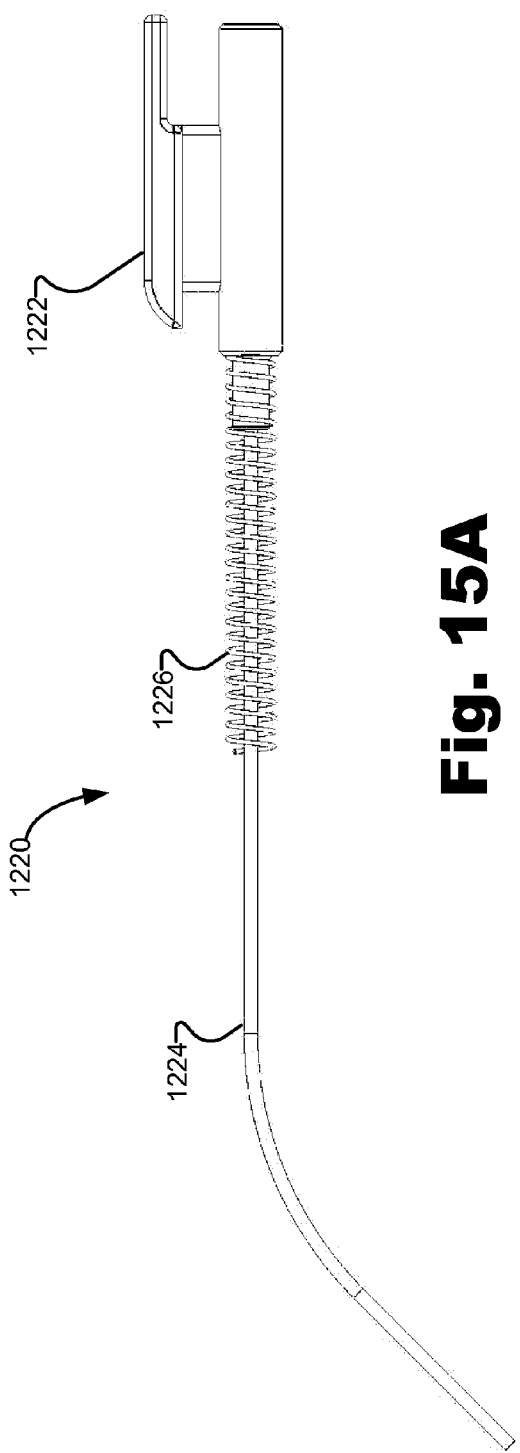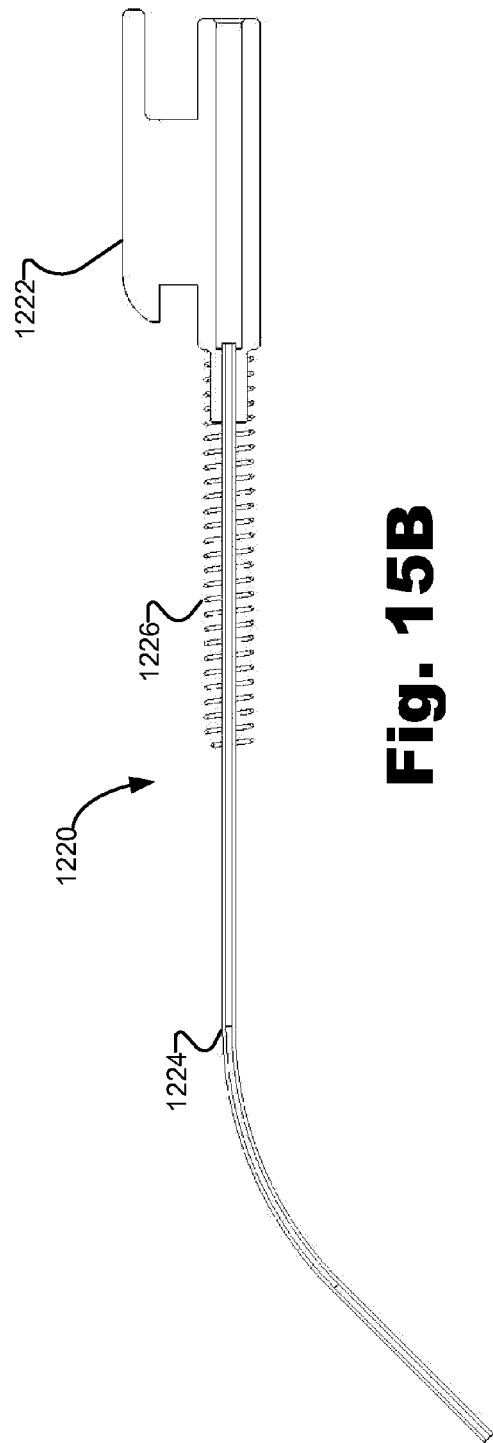

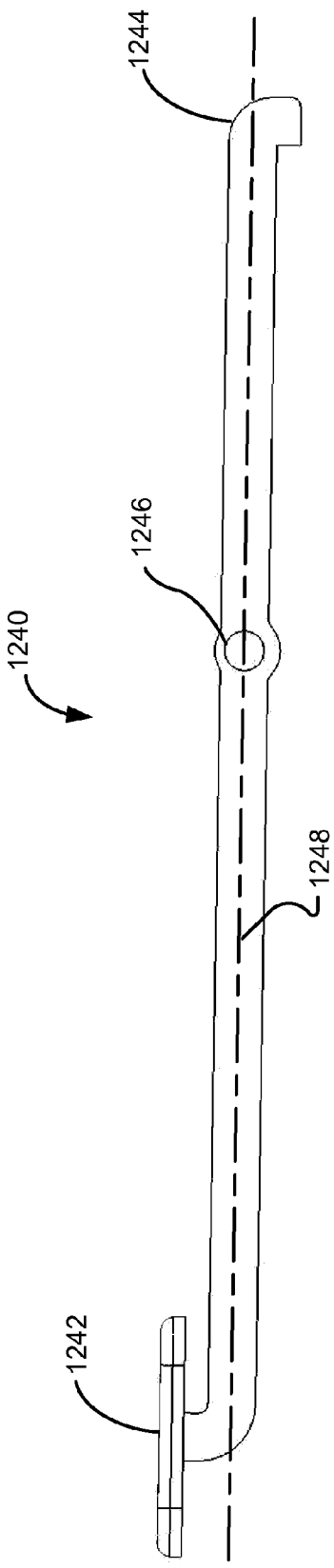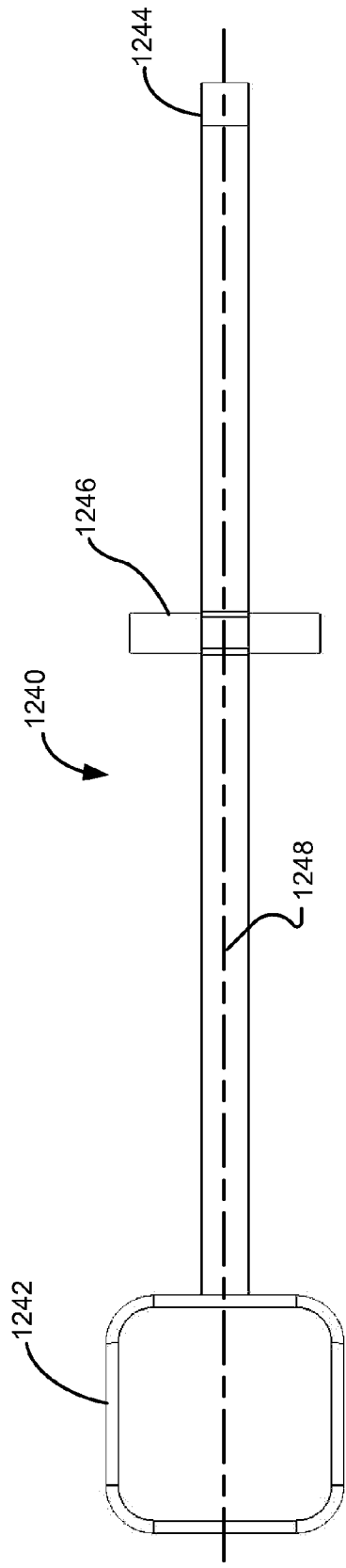
Fig. 17A
Fig. 17B

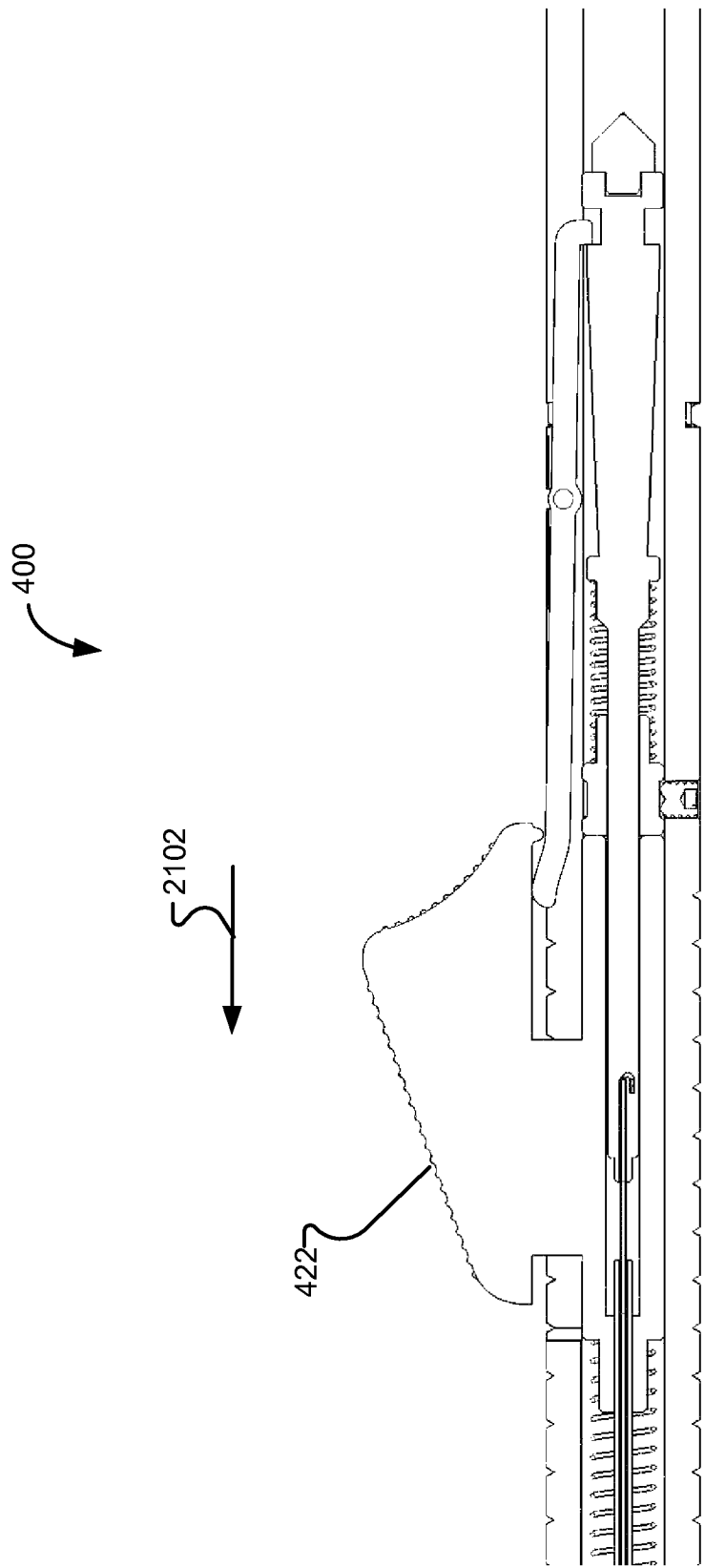

TOOLS, SYSTEMS, AND METHODS FOR INSERTING AN ELECTRODE ARRAY PORTION OF A LEAD INTO A BODILY ORIFICE

BACKGROUND

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an electrode array portion of a lead may be implanted in the cochlea. Electrodes included on the electrode array portion form stimulation channels through which electrical stimulation pulses may be applied directly to auditory nerves within the cochlea. An audio signal may therefore be presented to a patient by translating the audio signal into electrical stimulation pulses and applying the stimulation pulses directly to auditory nerves within the cochlea via one or more of the electrodes.

The electrode array portion is often implanted within the scala tympani, one of three parallel ducts that make up the spiral-shaped cochlea. Electrode array portions that are implanted in the scala tympani typically include several separately connected stimulating electrodes (or "electrode contacts") longitudinally disposed on a thin, elongate, and flexible carrier. Such an electrode array portion is pushed into the scala tympani duct via a surgical opening made in the cochlea wall at or near the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible and/or to any other location (e.g., a mid-scalar location) as may serve a particular application. To this end, various electrode array portions have been developed that have resilient carriers configured to better conform to the shape of the scala tympani and/or other auditory structures.

Unfortunately, many conventional insertion tools used to insert electrode array portions into the cochlea are cumbersome and difficult to use. For example, it is often difficult to release an electrode array portion from an insertion tool once the electrode array portion has been inserted into the cochlea. In addition, a stiffening member (e.g., a stylet) may be used to facilitate insertion of the electrode array portion of a lead into the cochlea, and retracting the stiffening member from the electrode array portion may be difficult and tend to dislodge the electrode array portion out of position.

SUMMARY

An exemplary insertion tool configured to facilitate insertion of an electrode array portion of a lead into a bodily orifice includes a handle assembly configured to facilitate handling of the insertion tool, a slider assembly disposed at least partially within the handle assembly and configured to be actuated by a user to operate the insertion tool, a retractor assembly disposed at least partially within the handle assembly and comprising a stiffening member configured to be inserted into the electrode array portion and a spring-loaded retractor member coupled at a distal end to the stiffening member and configured to move from a distal position to a proximal position to at least partially retract the stiffening member from the electrode array portion, and a rocker lever configured to selectively retain the spring-loaded retractor member in the distal position and release the spring-loaded retractor member to move from the distal position to the proximal position in response to actuation by the user of the slider assembly or the rocker lever.

An exemplary system comprises a lead including an electrode array portion, and an insertion tool configured to facilitate insertion of the electrode array portion into a bodily orifice. The insertion tool includes a handle assembly configured to facilitate handling of the insertion tool, a slider assembly disposed at least partially within the handle assembly and configured to be actuated by a user to operate the insertion tool, a retractor assembly disposed at least partially within the handle assembly and comprising a stiffening member configured to be inserted into the electrode array portion and a spring-loaded retractor member coupled at a distal end to the stiffening member and configured to move from a distal position to a proximal position to at least partially retract the stiffening member from the electrode array portion, and a rocker lever configured to selectively retain the spring-loaded retractor member in the distal position and release the spring-loaded retractor member to move from the distal position to the proximal position in response to actuation by the user of the slider assembly or the rocker lever.

An exemplary method of inserting an electrode array portion of a lead into a bodily orifice includes coupling the lead to an insertion tool, guiding the electrode array portion into a bodily orifice with the insertion tool, and moving a slider member of the insertion tool from a first position to a second position to facilitate actuation of a rocker lever to release a spring-loaded retractor member to move from the distal position to the proximal position to at least partially retract a stiffening member from the electrode array portion.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 5A is a side view of the exemplary insertion tool of FIG. 4 according to principles described herein.

FIG. 5B is a cross-sectional side view of the exemplary insertion tool of FIG. 4 according to principles described herein.

FIG. 6A is a side view of an exemplary handle assembly of the exemplary insertion tool of FIG. 4 according to principles described herein.

FIG. 6B is a cross-sectional side view of the exemplary handle assembly of FIG. 6A according to principles described herein.

FIG. 7A is a side view of an exemplary slider assembly of the exemplary insertion tool of FIG. 4 according to principles described herein.

FIG. 7B is a cross-sectional side view of the exemplary slider assembly of FIG. 7A according to principles described herein.

FIG. 8A is a side view of an exemplary retractor assembly of the exemplary insertion tool of FIG. 4 according to principles described herein.

FIG. 8B is a cross-sectional side view of the exemplary retractor assembly of FIG. 8A according to principles described herein.

FIG. 9A is a side view of an exemplary rocker lever of the exemplary insertion tool of FIG. 4 according to principles described herein.

FIG. 9B is a top view of the exemplary rocker lever of FIG. 9A according to principles described herein.

FIG. 11A is a side view of an exemplary plunger assembly of the exemplary insertion tool of FIG. 4 according to principles described herein.

FIG. 11B is a cross-sectional side view of the exemplary plunger assembly of FIG. 11A according to principles described herein.

FIG. 13A is a side view of the exemplary insertion tool of FIG. 12 according to principles described herein.

FIG. 13B is a cross-sectional side view of the exemplary insertion tool of FIG. 12 according to principles described herein.

FIG. 14A is a side view of an exemplary handle assembly of the exemplary insertion tool of FIG. 12 according to principles described herein.

FIG. 14B is a cross-sectional side view of the exemplary handle assembly of FIG. 14A according to principles described herein.

FIG. 15A is a side view of an exemplary slider assembly of the exemplary insertion tool of FIG. 12 according to principles described herein.

FIG. 15B is a cross-sectional side view of the exemplary slider assembly of FIG. 15A according to principles described herein.

FIG. 17A is a side view of an exemplary rocker lever of the exemplary insertion tool of FIG. 12 according to principles described herein.

FIG. 17B is a top view of the exemplary rocker lever of FIG. 17A.

FIG. 21C shows a cross-sectional side view of an exemplary slider assembly of the exemplary insertion tool of FIG. 21A being moved in a distal direction according to principles described herein.

Throughout the drawings, identical reference numbers may designate similar, but not necessarily identical, elements.

DETAILED DESCRIPTION

Exemplary insertion tools, systems, and methods for inserting an electrode array portion of a lead into a bodily orifice are described herein. As used herein, the term "bodily orifice" refers to a duct of the cochlea, a surgically made opening or incision (e.g., a cochleostomy or facial recess) within the patient, or any other location within the patient. For illustrative purposes only, it will be assumed in the examples given that the insertion tools, systems, and methods described herein may be used to insert an electrode array portion of a lead into a duct of the cochlea via a cochleostomy.

In some examples, an exemplary insertion tool described herein includes a handle assembly, a slider assembly, a retractor assembly, a plunger assembly, and a rocker lever. The handle assembly may be configured to facilitate handling of the insertion tool. The slider assembly may be configured to be actuated by a user to operate the insertion tool. The retractor assembly may comprise a spring-loaded retractor member and a stiffening member coupled to a distal end of the spring-loaded retractor member and configured to be inserted into an electrode array portion of a lead. The retractor member may be configured to move from a distal position to a proximal position to at least partially retract the stiffening member from the electrode array portion. The rocker lever may be configured to selectively retain the spring-loaded retractor member in the distal position.

A number of advantages are associated with the insertion tools, systems, and methods described herein. For example, the insertion tools described herein may facilitate insertion of an electrode array portion of a lead into a duct of the cochlea. The insertion tools described herein may additionally or alternatively be used with either the right or left hand of a surgeon or other user to insert an electrode array portion into either a right or left cochlea and are configured to not obstruct the view of the user while inserting the electrode array portion into the cochlea. These and other advantages will be described in more detail below.

In the following description, for purposes of explanation, numerous specific details are set forth in order to provide a thorough understanding of the present tools, systems, and methods. It will be apparent, however, to one skilled in the art that the present tools, systems, and methods may be practiced without these specific details. Reference in the specification to "one embodiment," "an embodiment," "one example," or "an example" means that a particular feature, structure, or characteristic described in connection with the embodiment is included in at least one embodiment. The appearance of the phrase "in one embodiment" in various places in the specification are not necessarily all referring to the same embodiment.

Figure 1:
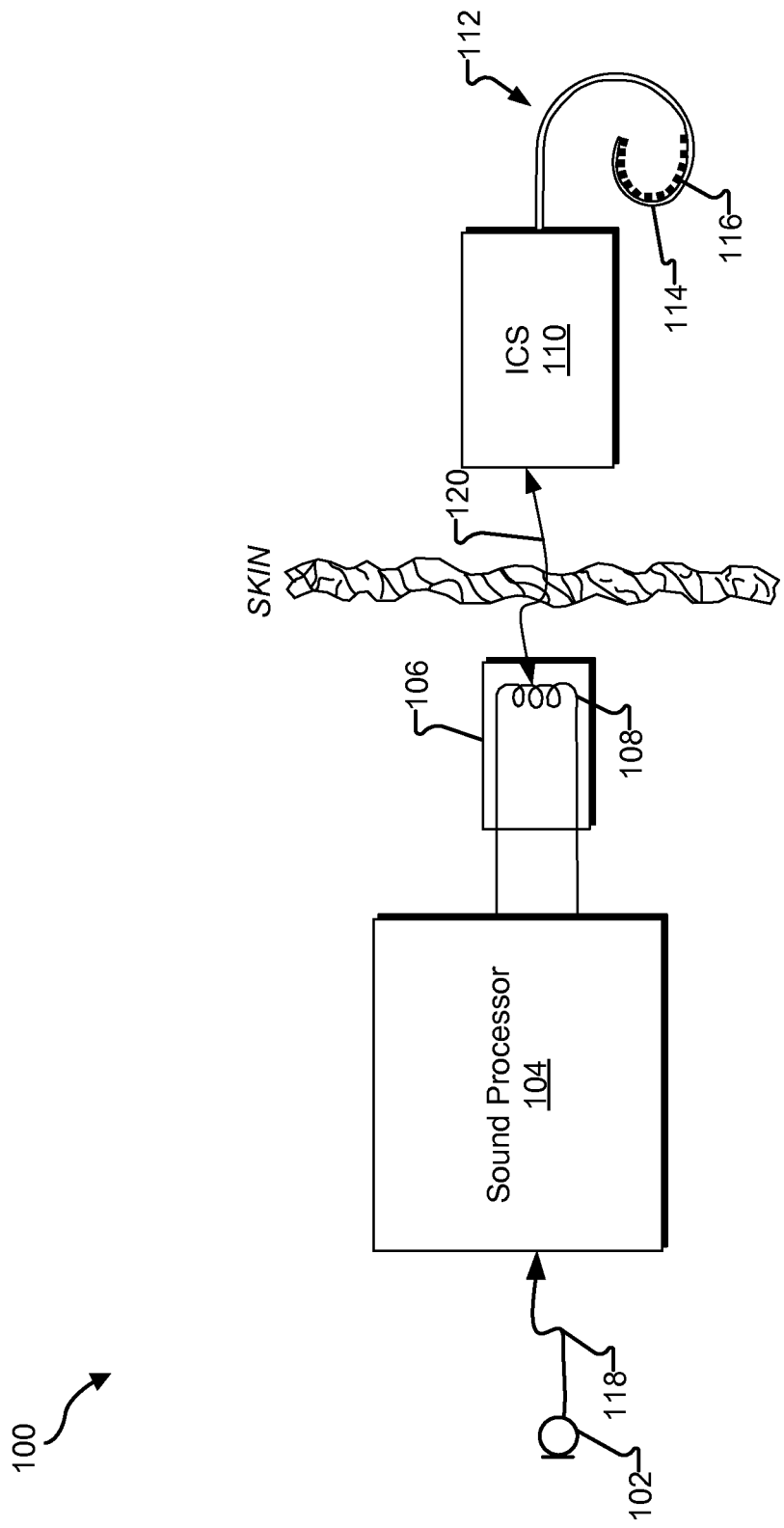
FIG. 1 illustrates an exemplary cochlear implant system according to principles described herein.

FIG. 1 illustrates an exemplary cochlear implant system 100. Cochlear implant system 100 may include a microphone 102, a sound processor 104, a headpiece 106 having a coil 108 disposed therein, an implantable cochlear stimulator ("ICS") 110, and a lead 112 having an electrode array portion 114 that comprises a plurality of electrodes 116. Additional or alternative components may be included within cochlear implant system 100 as may serve a particular application.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 118, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented within a behind-the-ear ("BTE") unit, a portable speech processor ("PSP"), and/or any other sound processing unit as may serve a particular application. Exemplary components of sound processor 104 will be described in more detail below.

Sound processor 104 may be configured to transcutaneously transmit one or more control parameters and/or one or more power signals to implantable cochlear stimulator 110 with coil 108 by way of communication link 120. These control parameters may be configured to specify one or more stimulation parameters, operating parameters, and/or any other parameter as may serve a particular application. Exemplary control parameters include, but are not limited to, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and back-end dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 120. It will be understood that data communication link 120 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 116 of electrode array portion 114 of lead 112.

To facilitate application of the electrical stimulation generated by implantable cochlear stimulator 110, electrode array portion 114 may be inserted within a duct of the cochlea such that electrodes 116 are in communication with one or more stimulation sites within the cochlea. As used herein, the term "in communication with" refers to electrodes 116 being adjacent to, in the general vicinity of, in close proximity to, directly next to, or directly on the stimulation site. Electrode array portion 114 may comprise any number of electrodes 116 (e.g., sixteen) as may serve a particular application.

Figure 2:
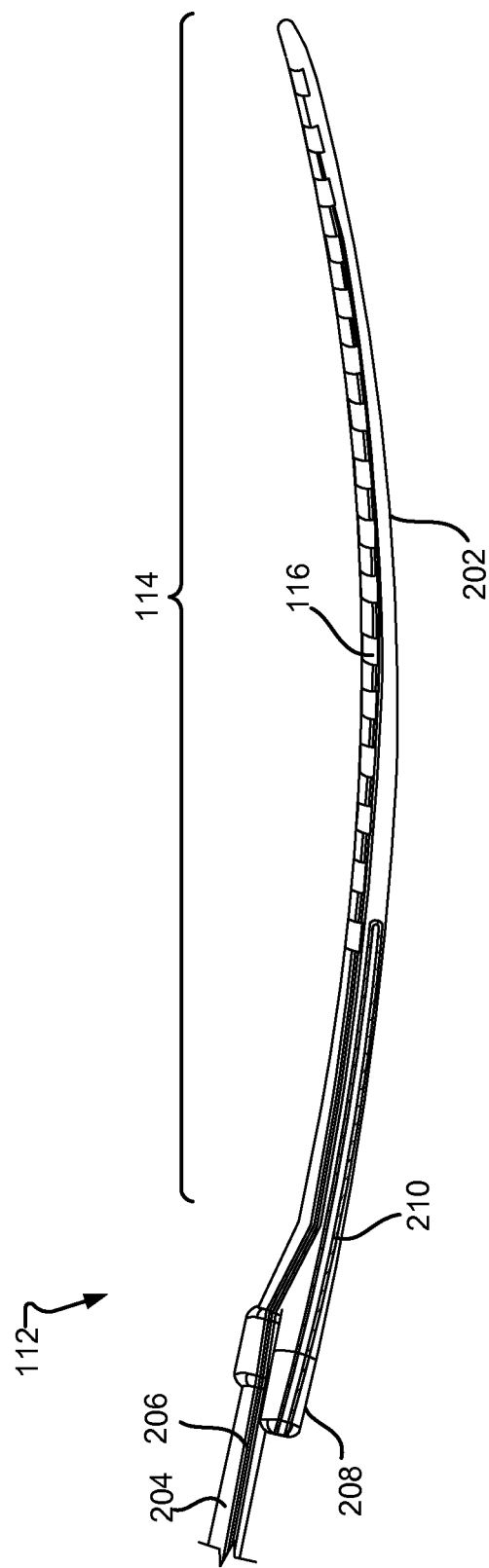
FIG. 2 illustrates an exemplary lead including an electrode array portion according to principles described herein.

FIG. 2 shows a side view of lead 112 including electrode array portion 114. Lead 112 may be substantially as shown and described in U.S. Pat. Nos. 4,819,647; 6,129,753; or 6,604,283, and in the U.S. patent application entitled "COCHLEAR IMPLANT SYSTEM WITH REMOVABLE STYLET" to Gallegos et al. filed Jun. 25, 2010, each of which is incorporated herein by reference in its respective entirety.

As shown, in some examples, lead 112 may include electrode array portion 114 having an array of electrodes 116 disposed on an elongate flexible carrier 202 (or simply "carrier 202"), a lead body 204 connected to a proximal end of carrier 202, insulated wires 206 disposed through lead body 204 (e.g., to connect electrodes 116 to implantable cochlear stimulator 110), and a molded feature 208 coupled to a proximal end of carrier 202 and configured to provide a structure that can couple to an insertion tool.

Elongate flexible carrier 202 may be made out of any suitable material such as, but not limited to, medical grade silicone rubber or plastic, and may include a lumen 210 passing at least partially therethrough. In some examples, carrier 202 may be tapered such that a distal portion (e.g., the portion common with electrode array portion 114) is thinner and, as a result, more flexible than a proximal portion. Carrier 202 may be configured to allow electrode array portion 114 to bend and conform to the geometry of a cochlea. In some examples, electrodes 116 of electrode array portion 114 may be configured to be positioned along a medial electrode wall (e.g., along the inside curve of carrier 202) such that they face the modiolus when implanted in the cochlea. Accordingly, electrode array portion 114 may be inserted into the scala tympani of the cochlea, thereby bringing electrodes 116 into close proximity with the auditory nerve tissue of the cochlea.

Lumen 210 may have any suitable length and may extend at least partially through carrier 202 and/or electrode array portion 114 to any of a variety of locations. In some examples, lumen 210 may be configured to receive a stiffening member (e.g., a stylet) to facilitate insertion of electrode array portion 114 into a cochlea, as will be explained in more detail below.

Figure 3:
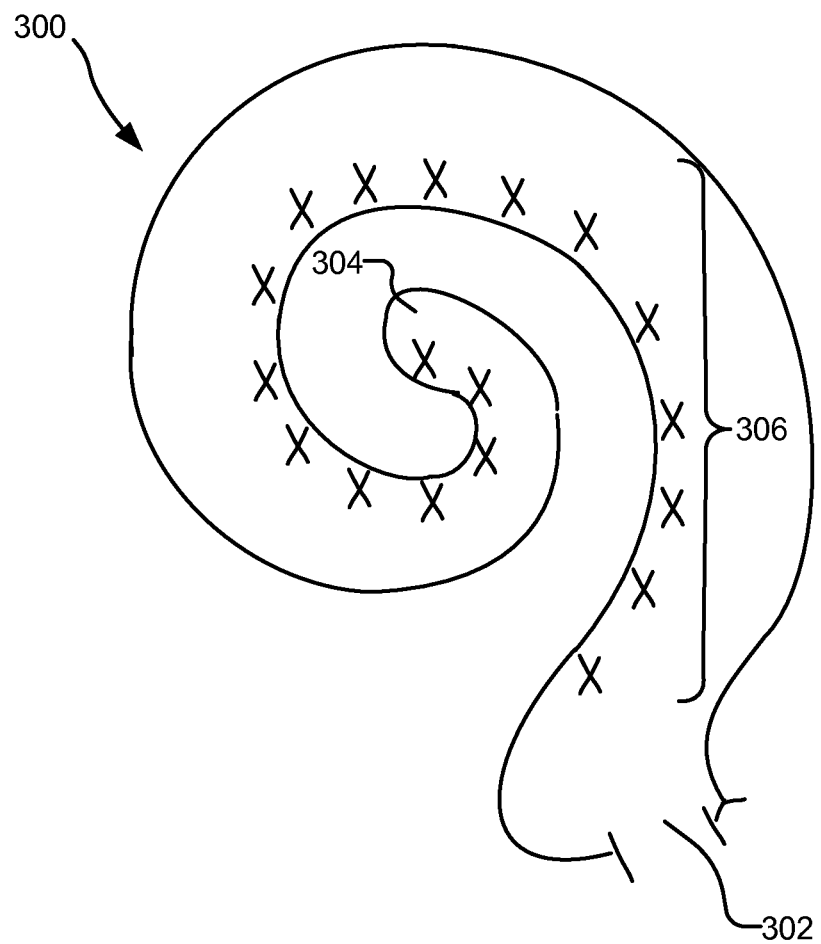
FIG. 3 illustrates a schematic structure of a human cochlea.

FIG. 3 illustrates a schematic structure of the human cochlea 300 into which electrode array portion 114 may be inserted. As shown in FIG. 3, the cochlea 300 is in the shape of a spiral beginning at a base 302 and ending at an apex 304. Within the cochlea 300 resides auditory nerve tissue 306, which is denoted by Xs in FIG. 3. The auditory nerve tissue 306 is organized within the cochlea 300 in a tonotopic manner. Low frequencies are encoded at the apex 304 of the cochlea 300 while high frequencies are encoded at the base 302. Hence, each location along the length of the cochlea 300 corresponds to a different perceived frequency. System 100 may therefore be configured to apply electrical stimulation to different locations within the cochlea 300 (e.g., different locations along the auditory nerve tissue 306) to provide a sensation of hearing.

Figure 4:
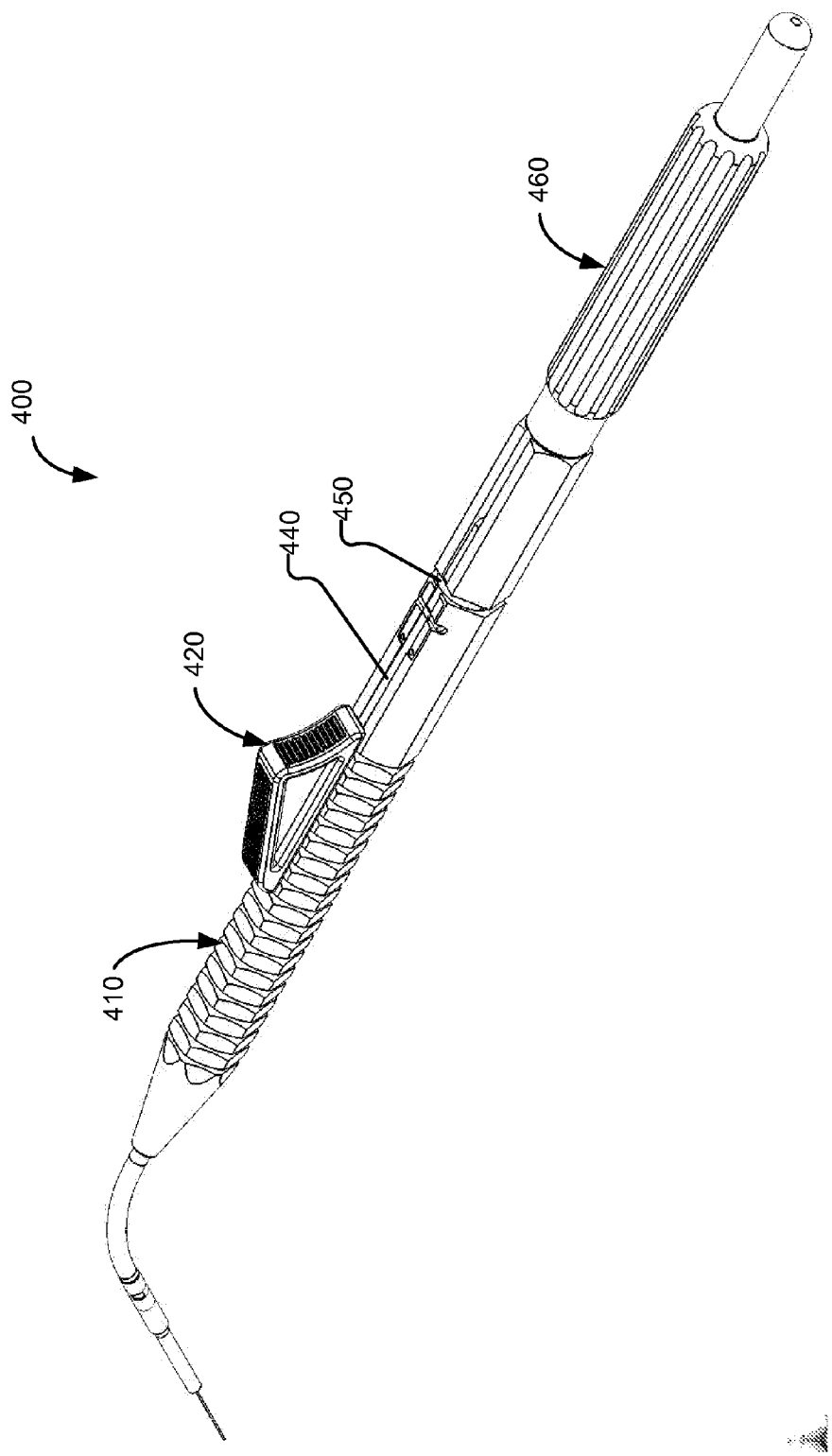
FIG. 4 is a perspective view of an exemplary insertion tool according to principles described herein.

FIG. 4 is a perspective view of an exemplary insertion tool 400 configured to facilitate insertion of an electrode array portion of a lead into a bodily orifice according to principles described herein. FIG. 5A is a side-view of insertion tool 400, and FIG. 5B is a cross-sectional side view of insertion tool 400. As shown, insertion tool 400 may include a handle assembly 410, a slider assembly 420 disposed at least partially within and slidable relative to handle assembly 410, a retractor assembly 430 disposed at least partially within handle assembly 410 and/or slider assembly 420, a rocker lever 440 coupled to handle assembly 410, a radial spring 450 disposed at least partially around handle assembly 410, and/or a plunger assembly 460 coupled to a proximal end of handle assembly 410. Each of the components of insertion tool 400 and the interaction between the components of insertion tool 400 will now be described in more detail.

As mentioned above, insertion tool 400 may include handle assembly 410. Handle assembly 410 may be configured to facilitate handling of insertion tool 400 by a user (e.g., a surgeon) and/or contain one or more other components of insertion tool 400. Handle assembly 410 is shown in more detail in FIG. 6A, which illustrates a side view of handle assembly 410, and FIG. 6B, which illustrates a cross-sectional side view of handle assembly 410.

As shown, handle assembly 410 may include a handle portion 411, a guide tube 412 coupled to a distal end of the handle portion 411, and a holder member 413 coupled to a distal end of guide tube 412. Handle portion 411 may be configured to be gripped and/or handled by a user (e.g., a surgeon) of insertion tool 400 and may contain one or more other components of insertion tool 400. In some examples, handle portion 411 may have a hexagonal cross-section to facilitate optimal gripping thereof by a user. Handle portion 411 may have a generally elongate shape and may be generally tubular with a lumen extending at least partially therethrough. In this manner, one or more other components of insertion tool 400 (e.g., retractor assembly 430 and/or slider assembly 420) may be disposed at least partially within and/or slide relative to handle portion 411, as will be explained in more detail below.

Handle portion 411 may include one or more other features configured to facilitate coupling and/or interaction between handle portion 411 and one or more other components of insertion tool 400. For example, handle portion 411 may include a handle slot 414 extending along a length thereof and configured to allow one or more components of insertion tool to extend through handle slot 414 and/or move relative to handle portion 411 within handle slot 414. In certain examples, a portion of slider assembly 420 may pass through handle slot 414 and may be configured to slide along handle slot 414 relative to handle portion 411 to facilitate actuation of slider assembly 420 by a user. In some embodiments, rocker lever 440 may be at least partially disposed within handle slot 414 and move (e.g., pivot) relative to handle portion 411. Additionally or alternatively, handle portion 411 may include a rocker lever recess 415 configured to receive at least a portion of rocker lever 440 and facilitate pivoting of rocker lever 440 relative to handle portion 411 and a radial spring recess 416 disposed at least partially around handle portion 411 and configured to receive radial spring 450, as will be explained in more detail below.

Guide tube 412 may be coupled to a distal end of handle portion 411. Guide tube 412 may be coupled to handle portion 411 in any suitable manner as may serve a particular implementation. For example, guide tube 412 may be welded, glued, or otherwise coupled to handle portion 411. Alternatively, guide tube 412 and handle portion 411 may be integrally formed together.

Guide tube 412 may be configured to at least partially contain one or more other components of insertion tool 400. For example, guide tube 412 may include a lumen extending along at least a length thereof and in communication with the lumen of handle portion 411. In some examples, portions of slider assembly 420 and/or retractor assembly 430 may be at least partially disposed within and slidable relative to guide tube 412, as will be described in more detail below.

As shown, guide tube 412 may include a curved portion such that a distal portion of guide tube 412 extends away from handle portion 411 at a predefined angle. Guide tube 412 may extend away from handle portion 411 at any suitable angle (e.g., approximately 45 degrees) as may serve a particular implementation. In certain embodiments, the angle of guide tube 412 may prevent handle portion 411 from obscuring the view of a user (e.g., a surgeon) as the user utilizes insertion tool 400 to insert an electrode array portion into a bodily orifice.

Holder member 413 may be configured to couple to a distal end of guide tube 412. For example, a proximal portion of holder member 413 may be configured to receive and couple to a distal portion of guide tube 412. Additionally or alternatively, holder member 413 may be configured to be rotatable relative to guide tube 412. Accordingly, a user may rotate holder member 413 relative to guide tube 412 as desired to facilitate the selective use of insertion tool 400 to insert an electrode array portion into a right or left cochlea.

In some examples, holder member 413 may be configured to removably couple to a lead (e.g., lead 112). For example, holder member 413 may include a lumen extending therethrough with a distal portion configured hold a portion of a lead proximal of the electrode array portion of the lead (e.g., molded feature 208). The lumen of holder member 413 may be in communication with the lumen of guide tube 412. Additionally or alternatively, holder member 413 may include a distal slot within a distal end thereof configured to hold a portion of a lead proximal of the electrode array portion of the lead (e.g., molded feature 208). In some examples, the distal slot may be configured to hold the lead and prevent relative rotation between holder member 413 and the lead.

Handle portion 411, guide tube 412, and/or holder member 413 may be made out of any rigid material as may serve a particular implementation. For example, handle portion 411, guide tube 412, and/or holder member 413 may be made out of stainless steel, titanium, a hard plastic, any other suitable material, and/or combinations thereof as may serve a particular implementation.

Handle portion 411, guide tube 412, and holder member 413 are provided for illustrative purposes only and are not limiting. Handle assembly 410 may include additional or alternative elements and/or may exclude certain illustrated elements according to principles described herein.

Returning to FIGS. 4, 5A, and 5B, insertion tool 400 may include slider assembly 420 disposed at least partially within and slidable relative to handle assembly 410. Slider assembly 420 may be configured to be actuated by a user to operate insertion tool 400. For example, slider assembly 420 may be configured to be actuated by a user to facilitate retraction of a stiffening member from an electrode array portion of a lead.

Slider assembly 420 is shown in greater detail in FIG. 7A, which illustrates a side view of slider assembly 420, and FIG. 7B, which illustrates a cross-sectional side view of slider assembly 420. As shown, slider assembly 420 may include a slider member 422, a tubular member 424 coupled to a distal end of slider member 422, and/or a spring member 426 coupled to slider member 422.

Slider member 422, tubular member 424, and/or spring member 426 may be coupled together in any suitable manner as may serve a particular implementation. For example, slider member 422, tubular member 424, and/or spring member 426 may be welded, glued, or otherwise coupled together. Alternatively, slider member 422, tubular member 424, and/or spring member 426 may be integrally formed together.

Slider member 422 may be configured to be actuated (e.g., advanced in a distal direction relative to handle assembly 410) by a user to perform one or more of the functions of insertion tool 400 described herein. For example, slider member 422 may be at least partially disposed within and slidable relative to handle portion 411. In certain embodiments, a portion of slider member 422 may be disposed within the lumen of handle portion 411 while another portion of slider member 422 may extend through handle slot 414 and out of handle portion 411 to facilitate actuation of slider member 422 by a user.

Slider member 422 may include one or more features configured to facilitate actuation by a user. For example, slider member 422 may include grooves or ridges disposed along a surface thereof configured to promote friction between a user's fingers or thumb and slider member 422. Additionally or alternatively, the shape of slider member 422 may conform to the shape of a user's finger or thumb to facilitate gripping and actuation of slider member 422. Slider member 422 may include any other features configured to facilitate actuation of slider member 422 by a user as may be suitable for a particular implementation.

In some examples, slider member 422 may be configured to slide relative to handle assembly 410 between a first position and a second position. A user may selectively actuate slider member 422 to move slider member from the first position to the second position to perform one or more operations of the insertion tool 400 (e.g., at least partially retract a stiffening member from an electrode array portion of a lead). For examples, slider member 422 may be configured to engage and actuate rocker lever 440 as slider member 422 moves from the first position to the second position, as will be explained in greater detail below.

In certain embodiments, spring member 426 may be configured to return slider member 422 from the second position to the first position upon release of slider member 422 by the user. For example, a distal end of spring member 426 may be fixed to handle portion 411. As a result, spring member 426 may compress as slider member 422 moves from the first position to the second position. The energy stored in spring member 426 may move slider member 422 from the second position back to the first position when slider member 422 is released by the user.

Slider member 422 may be configured to provide tactile feedback to a user. For example, slider member 422 may be configured to engage a detent (e.g., within or extending from handle portion 411) configured to resist movement of slider member 422 from the first position. As a result, engagement of the detent by slider member 422 may allow a user to feel when slider member 422 is in the first position.

Slider member 422 may be configured to contain one or more other components of insertion tool 400. For example, slider member 422 may include a lumen extending therethrough, within which one or more other components of insertion tool 400 may be disposed. In some examples, retractor assembly 430 may be at least partially disposed through and slidable relative to slider member 422, as will be explained in more detail below.

Slider member 422 may be made out of any suitable material as may serve a particular implementation. For example, slider member 422 may be made out of one or more rigid materials, such as stainless steel, titanium, a hard plastic, any other suitable material, or combinations thereof.

Tubular member 424 may be configured to contain one or more other components of insertion tool 400. For example, tubular member 424 may include a lumen extending therethrough and in communication with the lumen of slider member 422. In some examples, retractor assembly 430 may be disposed at least partially within and slidable relative to tubular member 424, as will be explained in more detail below.

Tubular member 424 may be made out of any suitable material as may serve a particular implementation. For example, tubular member 424 may be made out of one or more semi-rigid or flexible materials, such as PTFE or any other suitable material as may serve a particular implementation.

Slider member 422, tubular member 424, and/or spring member 426 are provided for illustrative purposes only and are not limiting. One will appreciate that slider assembly 420 may include additional or alternative elements and/or may exclude certain illustrated elements according to principles described herein.

Returning to FIG. 5B, as shown, insertion tool 400 may include a retractor assembly 430 disposed at least partially within and slidable relative to handle assembly 410 and/or slider assembly 420. As will be explained in more detail below, retractor assembly 430 may include a stiffening member and may be configured to at least partially retract the stiffening member from an electrode array portion in response to actuation by a user of slider assembly 420.

Retractor assembly 430 is shown in greater detail in FIG. 8A, which illustrates a side view of retractor assembly 430, and FIG. 8B, which illustrates a cross-sectional side view of retractor assembly 430. As shown, retractor assembly 430 may include a retractor member 431, a stiffening member 432 coupled to and extending from a distal end of retractor member 431, a spring member 433 coupled to retractor member 431, and a sleeve member 434 coupled to a distal end of spring member 433.

Retractor member 431, stiffening member 432, spring member 433, and/or sleeve member 434 may be coupled together in any suitable manner as may serve a particular implementation. For example, retractor member 431, stiffening member 432, spring member 433, and/or sleeve member 434 may be welded, glued, or otherwise coupled together. Alternatively, retractor member 431, stiffening member 432, spring member 433, and/or sleeve member 434 may be integrally formed together.

Stiffening member 432 may be configured to insert at least partially into an electrode array portion of a lead (e.g., into electrode array portion 114 of lead 112) to assist in the insertion of the electrode array portion into a cochlea. For example, a distal end of stiffening member 432 may be configured to be inserted into a lumen within the electrode array portion to provide sufficient stability to insert the electrode array portion into the cochlea. In some examples, stiffening member 432 may be configured to include and/or have the characteristics of a stylet.

Stiffening member 432 may be made out of any suitable material with sufficient stiffness so as to facilitate entry of an electrode array portion into the cochlea. For example, stiffening member 432 may be made out of a metal (e.g., stainless steel or titanium), a metal alloy, a hard plastic, any other suitable material, and/or combinations thereof.

As shown, stiffening member 432 may be fixedly coupled to a distal end of retractor member 431. However, in alternative examples, stiffening member 432 and retractor member 431 may be configured to be removably coupled together such that a user may choose to uncouple and/or re-couple stiffening member 432 and retractor member 431 as may be suitable for a particular implementation.

Retractor member 431 may be configured to slide relative to handle assembly 410 to at least partially retract stiffening member 432 from an electrode array portion of a lead. For example, retractor member 431 may be configured to be slidable relative to handle assembly 410 and/or slider assembly 420 from a distal position to a proximal position to at least partially retract stiffening member 432 from the electrode array portion.

In some examples, retractor member 431 may be configured to move from the distal position to the proximal position in response to actuation by a user of slider assembly 420. For example, as will be explained in more detail below, retractor member 431 may be retained in a distal position by one or more other components of insertion tool 400. While retractor member 431 is retained in the distal position, spring member 433 may be configured to store sufficient energy (e.g., in a compressed position) to move retractor member 431 from the distal position to the proximal position. Upon release of retractor member 431, spring member 433 may release the stored energy (e.g., elongate) to move retractor member 431 and, as a result, stiffening member 432 from the distal position to the proximal position to at least partially retract stiffening member 423 from the electrode array portion. In some examples, a distal end of spring member 433 may be fixed relative to handle assembly 410 to facilitate movement of retractor member 431. For example, a distal end of spring member 433 may be coupled to sleeve member 434, which may be fixed relative to handle portion 411 in any suitable manner as may serve a particular implementation.

Retractor member 431 may include an annular recess 435 configured to be selectively engaged by one or more other components of insertion tool 400 to retain retractor member 431 in the distal position. For examples, annular recess 435 may be configured to be engaged by a portion of rocker lever 440, as will be explained in more detail below. Retractor member 431 may also include a shock absorber 436 configured to absorb energy created by contact between retractor assembly 430 and one or more other components of insertion tool 400 (e.g., plunger assembly 460), as will be described in more detail below.

Retractor member 431, spring member 433, and/or sleeve member 434 may be made out of any suitable material as may serve a particular implementation. For example, retractor member 431, spring member 433, and/or sleeve member 434 may be made out of stainless steel, titanium, a hard plastic, any other suitable material, and/or combinations thereof.

Returning to FIGS. 4, 5A, and 5B, insertion tool 400 may include a rocker lever 440 pivotably coupled to handle assembly 410 (e.g., to handle portion 411). Rocker lever 440 may be configured to selectively engage retractor member 431 to retain retractor member 431 in a distal position and, in response to actuation by a user of slider member 422, release retractor member 431 to move from the distal position to the proximal position to at least partially retract stiffening member 432 from an electrode array portion of a lead.

Rocker lever 440 is shown in more detail in FIG. 9A, which illustrates a side view of rocker lever 440, and FIG. 9B, which illustrates a top view of rocker lever 440. As shown, rocker lever 440 may be generally elongate in shape and may include a distal portion 442, a proximal portion 444, and an axle 446. In some examples, rocker lever 440 may extend generally along a longitudinal axis 448.

Distal portion 442 may be configured to be engaged by slider member 422 to pivot rocker lever 440 about axle 446. For example, distal portion 442 may angle upwards away from longitudinal axis 448. In this manner, distal portion 442 may extend upwards out of handle portion 411 so as to be engaged by slider member 422 as slider member 422 moves from a first position to a second position.

Additionally or alternatively, proximal portion 444 may be configured to engage retractor member 431. For example, proximal portion 444 may include a bend in rocker lever 440 extending away from longitudinal axis 448 at approximately a right angle and may be configured to engage (e.g., partially insert into) annular recess 435 of retractor member 431 to retain retractor member 431 in a distal position.

Rocker lever 440 may be configured to pivot about axle 446. For example, axle 446 may be configured to be disposed within and pivot relative to rocker lever recess 415 of handle portion 411. As a result, rocker lever 440 may pivot in a first direction to engage retractor member 431 with proximal portion 444 to retain retractor member 431 in a distal position. Additionally or alternatively, slider member 422 may be configured to engage distal portion 442 to pivot rocker lever 440 in a second direction opposite the first direction causing proximal portion 444 to disengage and release retractor member 431 to allow retractor member 431 to move from the distal position to a proximal position (e.g., to at least partially retract stiffening member 432 from an electrode array portion of a lead).

Rocker lever 440 may be made out of any suitable material as may serve a particular implementation. For example, rocker lever 440 may be made out of one or more rigid materials, such as stainless steel, titanium, a rigid plastic, any other suitable rigid material, or combinations thereof as may serve a particular implementation.

Figure 10:
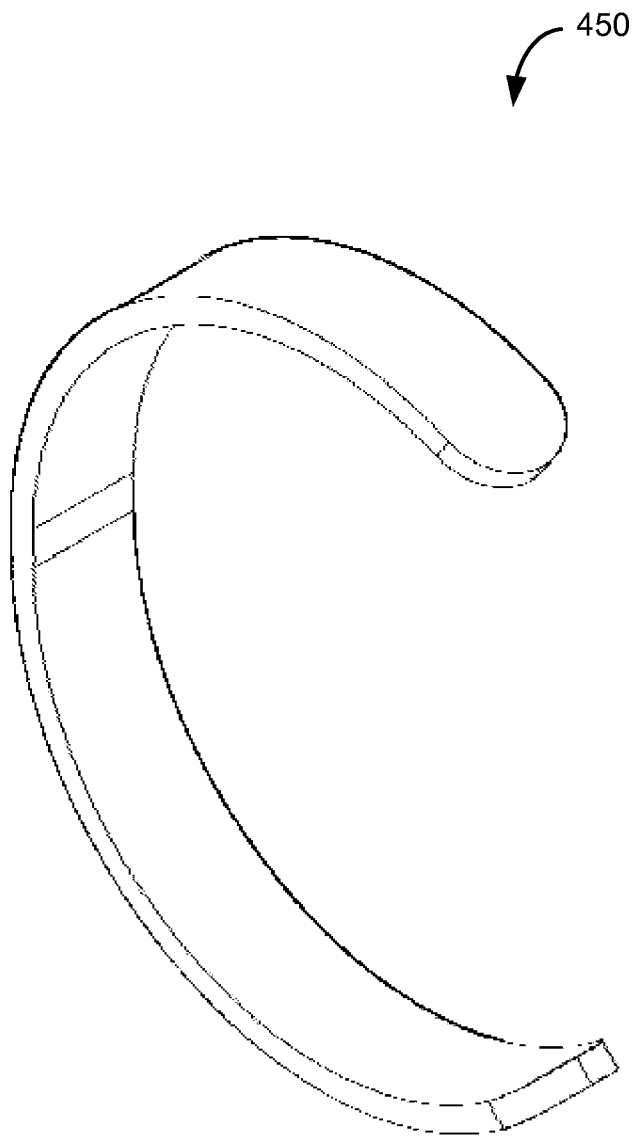
FIG. 10 is a perspective view of an exemplary radial spring of the exemplary insertion tool of FIG. 4 according to principles described herein.

Returning to FIGS. 4, 5A, and 5B, insertion tool 400 may include a radial spring 450 disposed at least partially around handle assembly 410. Radial spring 450 is shown in greater detail in FIG. 10. Radial spring 450 may be configured to engage rocker lever 440 and move rocker lever 440 into engagement with retractor member 431. For example, radial spring 450 may be configured to apply a constant force on rocker lever 440 to pivot rocker lever 440 to engage retractor member 431 with proximal portion 444. The force applied by radial spring 450 may be selectively overcome by actuation of slider member 422 by a user, thereby pivoting rocker lever 440 in the opposite direction to disengage and release retractor member 431.

As shown, radial spring 450 may have a C-shaped configuration and may be configured to extend around at least a portion of handle portion 411. In some examples, radial spring 450 may be configured to be disposed within radial spring recess 416 of handle portion 411.

Additionally or alternatively, radial spring 450 may be configured to have elastic properties. For example, radial spring 450 may be configured to elastically expand when rocker lever 440 is engaged and actuated by slider member 422 (e.g., to release retractor member 431) and then elastically contract when slider member 422 disengages rocker lever 440 to return rocker lever 440 to its original position (e.g., to engage retractor member 431).

Radial spring 450 may be made out of any suitable material as may serve a particular implementation. For example, radial spring 450 may be made out of one or more elastic materials, such as stainless steel, titanium, any other suitable material, or combinations thereof as may serve a particular implementation. In certain embodiments, the material of radial spring 450 may be spring tempered.

Returning to FIGS. 4, 5A, and 5B, insertion tool 400 may include a plunger assembly 460. Plunger assembly 460 may be configured to couple to a proximal end of handle assembly 410 and may be configured to be actuated by a user to reset retractor assembly 430 from a proximal position to a distal position.

Plunger assembly 460 is shown in greater detail in FIG. 11A, which illustrates a side view of plunger assembly 460, and 11B, which illustrates a cross-sectional side view of plunger assembly 460. As shown, plunger assembly 460 may include a plunger housing 462, a plunger member 464 disposed at least partially within and slidable relative to plunger housing 462, a button member 466 disposed at least partially through and slidable relative to plunger housing 462, and a spring member 468 with a distal end coupled to plunger housing 462 and a proximal end coupled to button member 466.

Plunger housing 462 may be configured to couple to handle portion 411 and at least partially contain plunger member 464, button member 466, and/or spring member 468. For example, plunger housing 462 may include a lumen extending along a length thereof and configured to at least partially contain plunger member 464, button member 466, and/or spring member 468.

Plunger member 464 may be configured to engage and reset retractor member 431. For example, plunger member 464 may be configured to slide relative to plunger housing 462 in response to actuation by a user of button member 466 to engage retractor member 431 to reset retractor member 431 from a proximal position to a distal position (e.g., where rocker lever 440 may retain retractor member 431), as will be explained in more detail below.

Button member 466 may be configured to be depressed by a user to advance plunger member 464 in a distal direction to engage and reset retractor member 431. After a user releases button member 466, spring member 468 may be configured to return button member 466 and plunger member 464 to their original position.

Plunger housing 462, plunger member 464, button member 466, and/or spring member 468 may be made out of any suitable materials as may serve a particular implementation. For example, plunger housing 462, plunger member 464, button member 466, and/or spring member 468 may be made out of stainless steel, titanium, a hard plastic, any other suitable material, and/or combinations thereof as may serve a particular implementation.

The components of insertion tool 400 are provided for illustrative purposes only and are not limiting. Insertion tool 400 may include additional or alternative elements and/or may exclude certain illustrated elements according to principles described herein.

Figure 12:
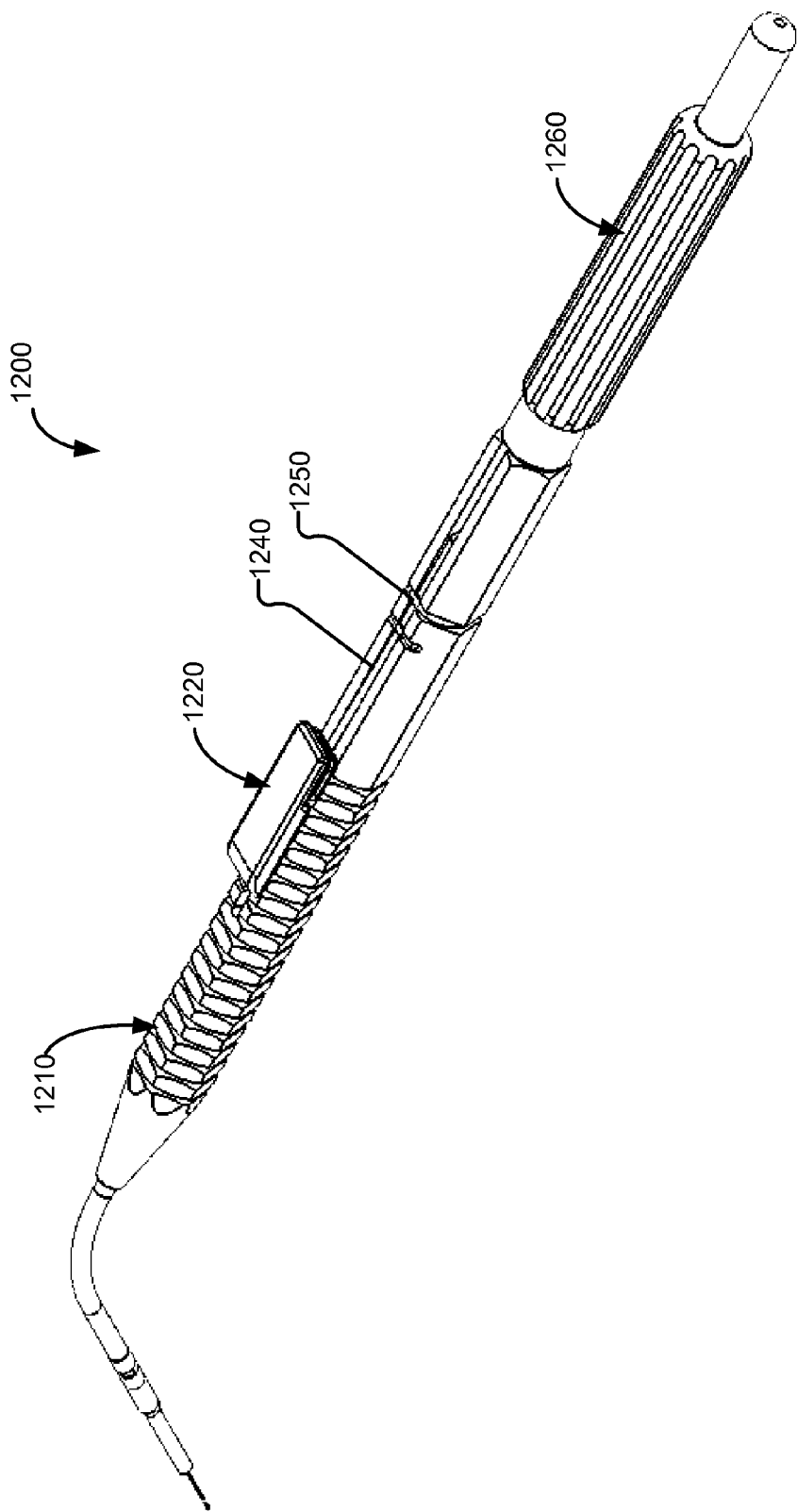
FIG. 12 is a perspective view of another exemplary insertion tool according to principles described herein.

FIG. 12 is a perspective view of another exemplary insertion tool 1200 configured to facilitate insertion of an electrode array portion of a lead into a bodily orifice according to principles described herein. Insertion tool 1200 may be similar in some respects to insertion 400 described herein. Accordingly, some aspects of insertion tool 1200 may not be described in detail with respect to this configuration as they are already described with respect to insertion tool 400. Like elements may be designated with like reference numerals.

FIG. 13A is a side-view of insertion tool 1200, and FIG. 13B is a cross-sectional side view of insertion tool 1200. As shown, insertion tool 1200 may include a handle assembly 1210, a slider assembly 1220 disposed at least partially within and slidable relative to handle assembly 1210, a retractor assembly 1230 disposed at least partially within handle assembly 1210 and/or slider assembly 1220, a rocker lever 1240 coupled to handle assembly 1210, a radial spring 1250 disposed at least partially around handle assembly 1210, and a plunger assembly 1260 coupled to a proximal end of handle assembly 1210. Each of the components of insertion tool 1200 and the interaction between the components of insertion tool 1200 will now be described in more detail.

As mentioned above, insertion tool 1200 may include handle assembly 1210. Handle assembly 1210 may be configured to facilitate handling of insertion tool 1200 by a user (e.g., a surgeon) and/or contain one or more other components of insertion tool 1200. Handle assembly 1210 is shown in more detail in FIG. 14A, which illustrates a side view of handle assembly 1210, and FIG. 14B, which illustrates a cross-sectional side view of handle assembly 1210. Handle assembly 1210 may be similar in many respects to handle assembly 410, described in more detail above.

For example, as shown, handle assembly 1210 may include a handle portion 1211, a guide tube 1212 coupled to a distal end of the handle portion 1211, and a holder member 1213 coupled to a distal end of guide tube 1212. Handle portion 1211 may be configured to be gripped and/or handled by a user (e.g., a surgeon) of insertion tool 1200 and may contain one or more other components of insertion tool 1200. In addition, handle portion 1211 may include a handle slot 1214 extending along a length thereof and configured to allow one or more components of insertion tool 1200 (e.g., slider assembly 1220) to extend through handle slot 1214 and/or move relative to handle portion 1211 within handle slot 1214. Additionally or alternatively, handle portion 1211 may include a rocker lever recess 1215 configured to receive at least a portion of rocker lever 1240 and facilitate pivoting of rocker lever 1240 relative to handle portion 1211 and a radial spring recess 1216 disposed at least partially around handle portion 1211 and configured to receive radial spring 1250.

Guide tube 1212 may be coupled to a distal end of handle portion 1211 and may be configured to at least partially contain one or more other components of insertion tool 1200. Additionally or alternatively, holder member 1213 may be coupled to a distal end of guide tube 1212 and configured to selectively couple to a lead, as described in more detail herein.

Returning to FIGS. 12, 13A, and 13B, insertion tool 1200 may include slider assembly 1220 disposed at least partially within and slidable relative to handle assembly 1210. Slider assembly 1220 may be configured to be actuated by a user to operate insertion tool 1200. For example, slider assembly 1220 may be configured to be actuated by a user to allow actuation of rocker lever 1240 to retract a stiffening member from an electrode array portion of a lead, as explained in more detail herein.

Slider assembly 1220 is shown in greater detail in FIG. 15A, which illustrates a side view of slider assembly 1220, and FIG. 15B, which illustrates a cross-sectional side view of slider assembly 1220. Slider assembly 1220 may be similar in some respects to slider assembly 420, described in more detail herein. For example, slider assembly 1220 may include a slider member 1222, a tubular member 1224 coupled to a distal end of slider member 1222, and a spring member 1226 coupled to slider member 1222.

Slider member 1222 may be configured to be actuated (e.g., advanced in a distal direction relative to handle assembly 1210) by a user to perform one or more of the functions of insertion tool 1200 described herein. For example, slider member 1222 may be configured to slide relative to handle assembly 1210 between a first position and a second position. In some examples, slider member 1222 may be configured to prevent inadvertent actuation of rocker lever 1240 when slider member 1222 is in the first position and allow actuation of rocker lever 1240 when slider member is in the second position. For example, slider member 1222 may be configured to at least partially cover rocker lever 1240 when in the first position and at least partially expose rocker lever 1240 when in the second position. As a result, a user may selectively actuate slider member 1222 to move slider member between the first position and the second position to allow actuation of rocker lever 1240, as will be explained in greater detail below.

Additionally or alternatively, spring member 1226 may be configured to return slider member 1222 from the second position to the first position when slider member 1222 is released by a user, as explained in more detail herein.

Returning to FIG. 13B, as shown, insertion tool 1200 may include a retractor assembly 1230 disposed at least partially within and slidable relative to handle assembly 1210 and/or slider assembly 1220. Retractor assembly 1230 may include a stiffening member configured to be inserted into an electrode array portion of a lead and retractor assembly 1230 may be configured to at least partially retract the stiffening member from the electrode array portion in response to actuation by a user of rocker lever 1240.

Figure 16A:
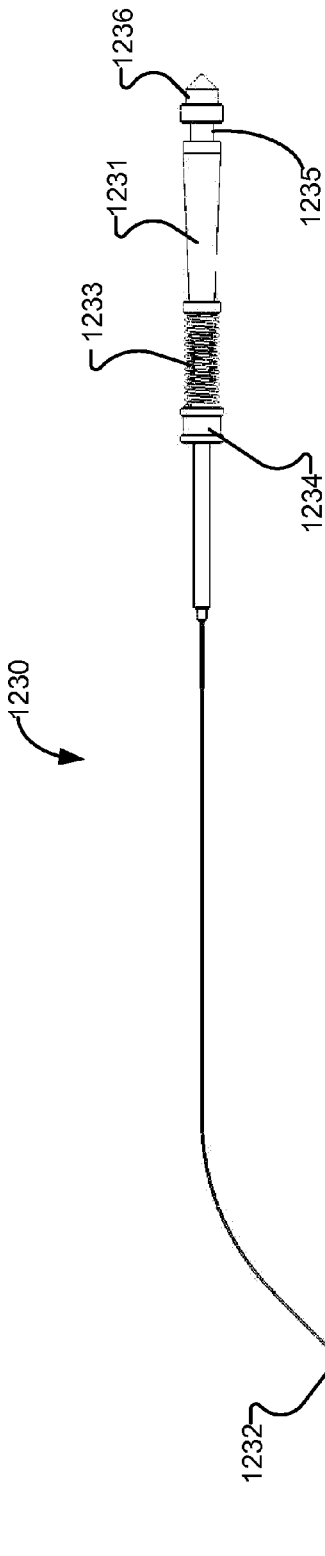
FIG. 16A is a side view of an exemplary retractor assembly of the exemplary insertion tool of FIG. 12 according to principles described herein.
Figure 16B:
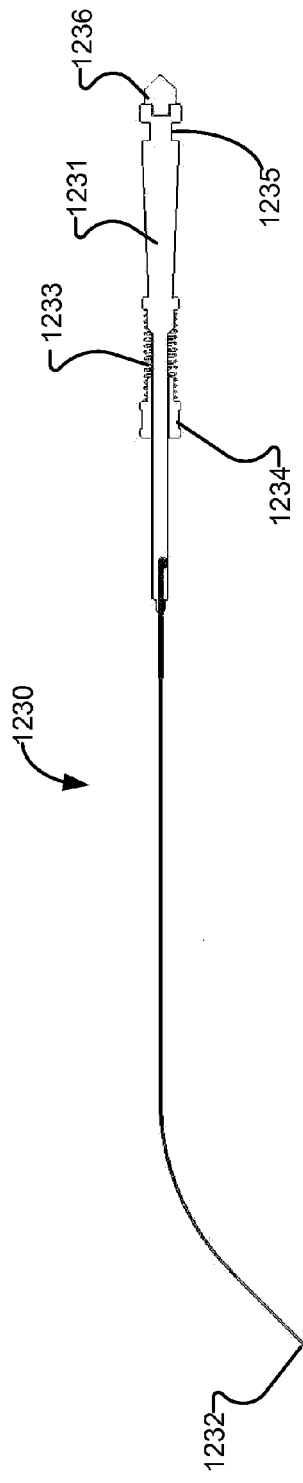
FIG. 16B is a cross-sectional side view of the exemplary retractor assembly of FIG. 16A according to principles described herein.

Retractor assembly 1230 is shown in greater detail in FIG. 16A, which illustrates a side view of retractor assembly 1230. Retractor assembly 1230 and may be similar in some respects to retractor assembly 430, described in more detail herein. For example, as shown, retractor assembly 1230 may include a retractor member 1231, a stiffening member 1232 coupled to and extending from a distal end of retractor member 1231, a spring member 1233 coupled to retractor member 1231, and a sleeve member 1234 coupled to a distal end of spring member 1233.

In some examples, a distal end of stiffening member 1232 may be configured to be inserted into an electrode array portion of a lead to provide sufficient stability to insert the electrode array portion into a cochlea. Retractor assembly 1230 may be configured to thereafter at least partially retract stiffening member 1232 from the electrode array portion. For example, retractor member 1231 may be configured to move from a distal position to a proximal position (e.g., by way of force exerted by spring member 1233) in response to actuation of a user of rocker lever 1240 to at least partially retract stiffening member 1232 from an electrode array portion of a lead. Additionally or alternatively, retractor member 1231 may include an annular recess 1235 configured to be engaged by rocker lever 1240 and a shock absorber 1236 configured to absorb energy created by contact between retractor assembly 1230 and one or more other components of insertion tool 1200 (e.g., plunger assembly 1260).

Returning to FIGS. 12, 13A, and 13B, insertion tool 1200 may include a rocker lever 1240 coupled to handle assembly 1210 (e.g., to handle portion 1211). Rocker lever 1240 may be configured to selectively engage retractor member 1231 to retain retractor member 1231 in a distal position and, in response to actuation by a user, release retractor member 1231 to move from the distal position to the proximal position to at least partially retract stiffening member 1232 from an electrode array portion of a lead.

Rocker lever 1240 is shown in more detail in FIG. 17A, which illustrates a side view of rocker lever 1240, and FIG. 17B, which illustrates a top view of rocker lever 1240. Rocker lever 1240 may be similar in some respects to rocker lever 440, described in more detail herein. For example, as shown, rocker lever 1240 may be generally elongate in shape and may include a distal portion 1242, a proximal portion 1244, and an axle 1246. In some examples, rocker lever 1240 may extend generally along a longitudinal axis 1248.

Distal portion 1242 may be configured to be engaged by a user (e.g., by a user's thumb or forefinger) to pivot rocker lever 1240 about axle 1246. For example, distal portion 1242 may extend upwards away from longitudinal axis 1248 and may include a pad or button configured to be pressed by a user to actuate rocker lever 1240. In some examples, slider member 1222 may be configured to cover distal portion 1242 when in the first position to prevent inadvertent actuation of rocker lever 1240 by a user and to at least partially expose distal portion 1242 when in the second position to allow actuation of rocker lever 1240 by the user.

Proximal portion 1244 may be configured to engage retractor member 1231 (e.g., engage annular recess 1235 of retractor member 1231) to retain retractor member 1231 in a distal position and disengage retractor member 1231 when rocker lever 1240 is actuated by a user to release retractor member 1231 to move from the distal position to a proximal position, as explained in more detail herein.

Figure 18:
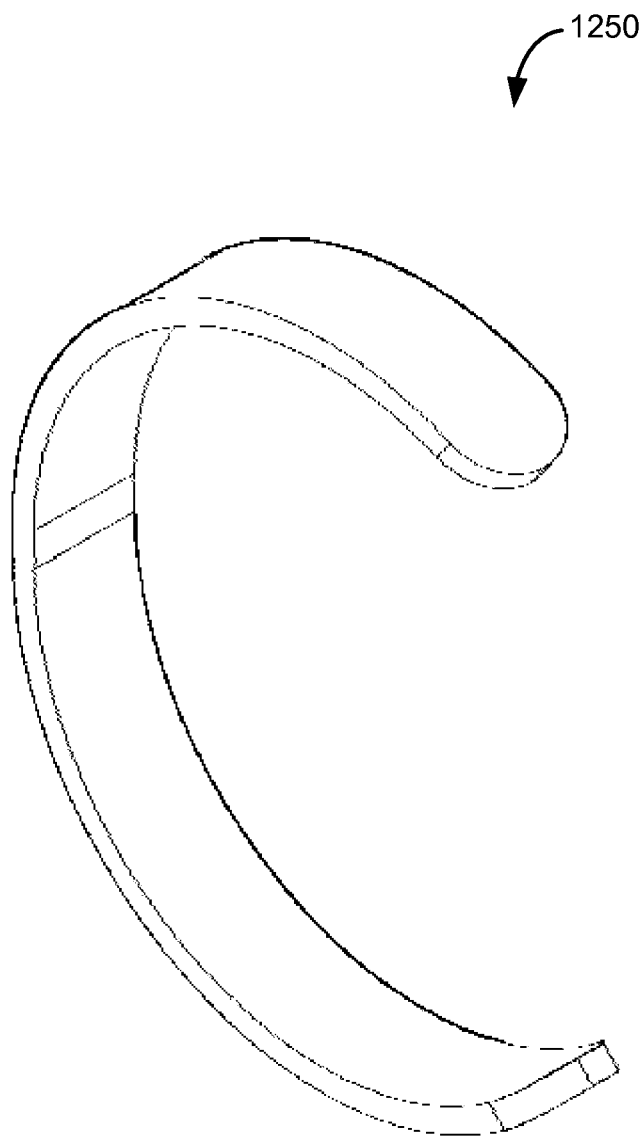
FIG. 18 is a perspective view of an exemplary radial spring of the exemplary insertion tool of FIG. 12 according to principles described herein.

Returning to FIGS. 12, 13A, and 13B, insertion tool 1200 may include a radial spring 1250 disposed at least partially around handle assembly 1210. Radial spring 1250 is shown in greater detail in FIG. 18. Radial spring 1250 may be similar in some respects to radial spring 450 of insertion tool 400. For example, radial spring 1250 may be configured to engage rocker lever 1240 to pivot rocker lever 1240 into engagement with retractor member 1231, as described in more detail herein.

Figure 19A:
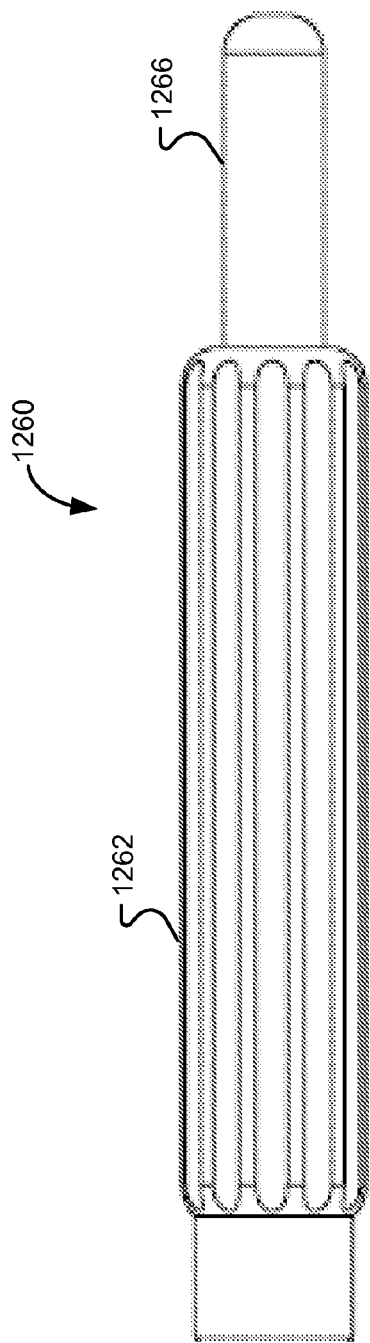
FIG. 19A is a side view of an exemplary plunger assembly of the exemplary insertion tool of FIG. 12 according to principles described herein.
Figure 19B:
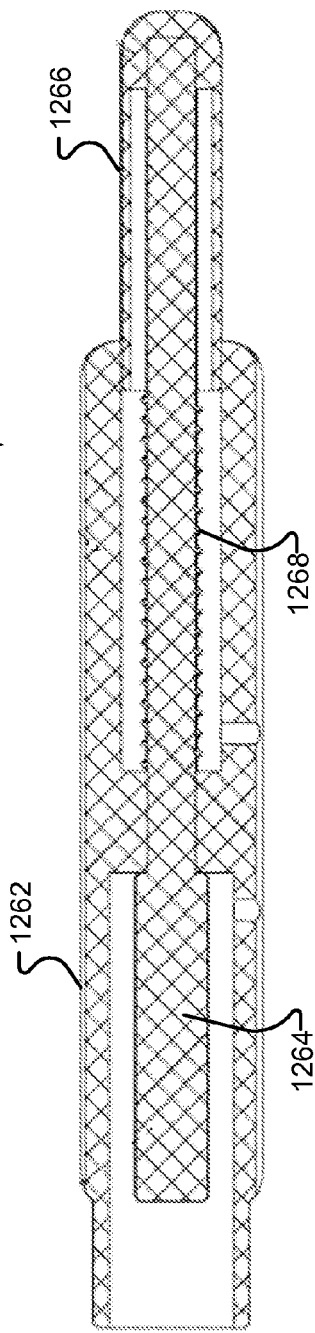
FIG. 19B is a cross-sectional side view of the exemplary plunger assembly of FIG. 11A according to principles described herein.

Returning to FIGS. 12, 13A, and 13B, insertion tool 1200 may include a plunger assembly 1260. Plunger assembly 1260 is shown in greater detail in FIG. 19A, which illustrates a side view of plunger assembly 1260, and 19B, which illustrates a cross-sectional side view of plunger assembly 1260. Plunger assembly 1260 may be similar in some respects to plunger assembly 460 of insertion tool 400. For example, as shown, plunger assembly 1260 may include a plunger housing 1262, a plunger member 1264 disposed at least partially through and slidable relative to plunger housing 1262, a button member 1266 disposed at least partially through and slidable relative to plunger housing 1262, and a spring member 1268 with a distal end coupled to plunger housing 1262 and a proximal end coupled to button member 1266. In some examples, plunger assembly 1260 may be configured to be actuated by a user to reset retractor assembly 1230 from a proximal position to a distal position, as explained in more detail above.

Figure 20:
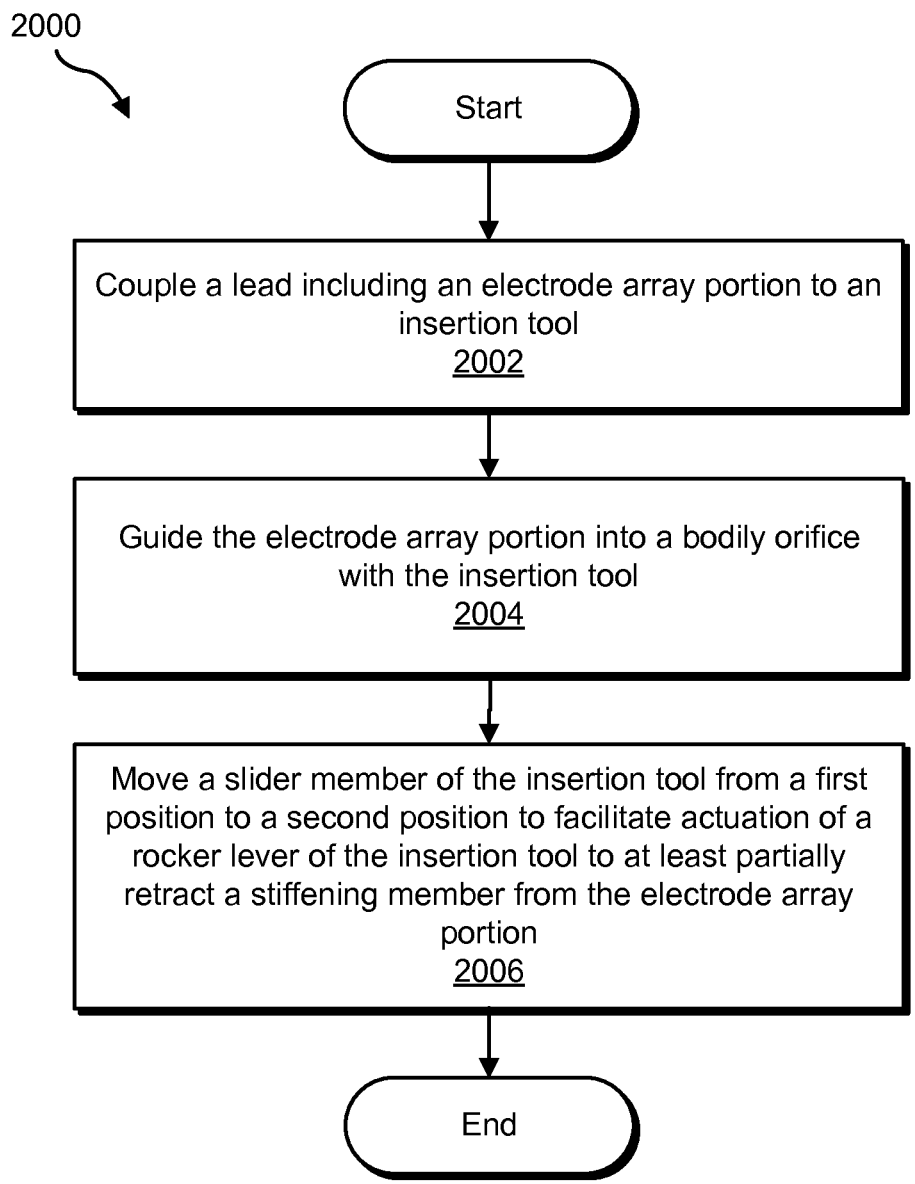
FIG. 20 illustrates an exemplary method of inserting an electrode array portion of a lead into a bodily orifice according to principles described herein.

FIG. 20 illustrates an exemplary method 2000 of inserting an electrode array portion of a lead into a bodily orifice. While FIG. 20 illustrates exemplary steps according to one embodiment, other embodiments may omit, add to, reorder, and/or modify any of the steps shown in FIG. 20.

Figure 21A:
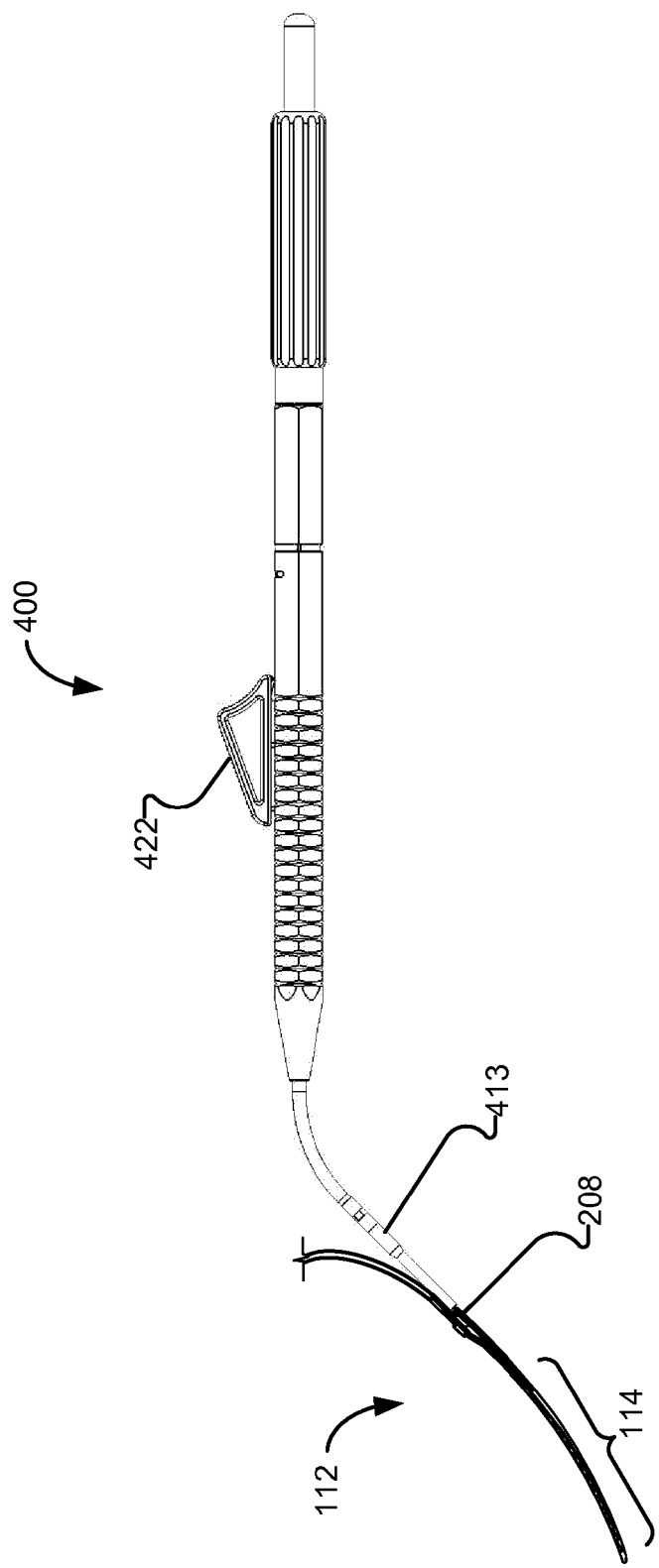
FIG. 21A shows an exemplary lead being coupled to an exemplary insertion tool according to principles described herein.

In step 2002, a lead including an electrode array portion may be coupled to an insertion tool. For example, FIG. 21A illustrates lead 112 coupled to insertion tool 400. Insertion tool 400 is shown for illustrative purposes only. In additional or alternative examples, any other insertion tool described herein (e.g., insertion tool 1200) may be utilized in accordance with method 2000.

In some examples, molded feature 208 of lead 112 may be removably coupled to holder member 413 and stiffening member 432 (FIGS. 8A and 8B) may be at least partially inserted into lead 112 (e.g., into lumen 210, FIG. 2). As shown in FIG. 21A, to facilitate coupling of stiffening member 300 to insertion tool 400, slider member 422 may be in a first position. While slider member 422 is in the first position, retractor member 431 (FIGS. 8A and 8B) may be retained in a distal position, as explained in more detail herein.

Figure 21B:
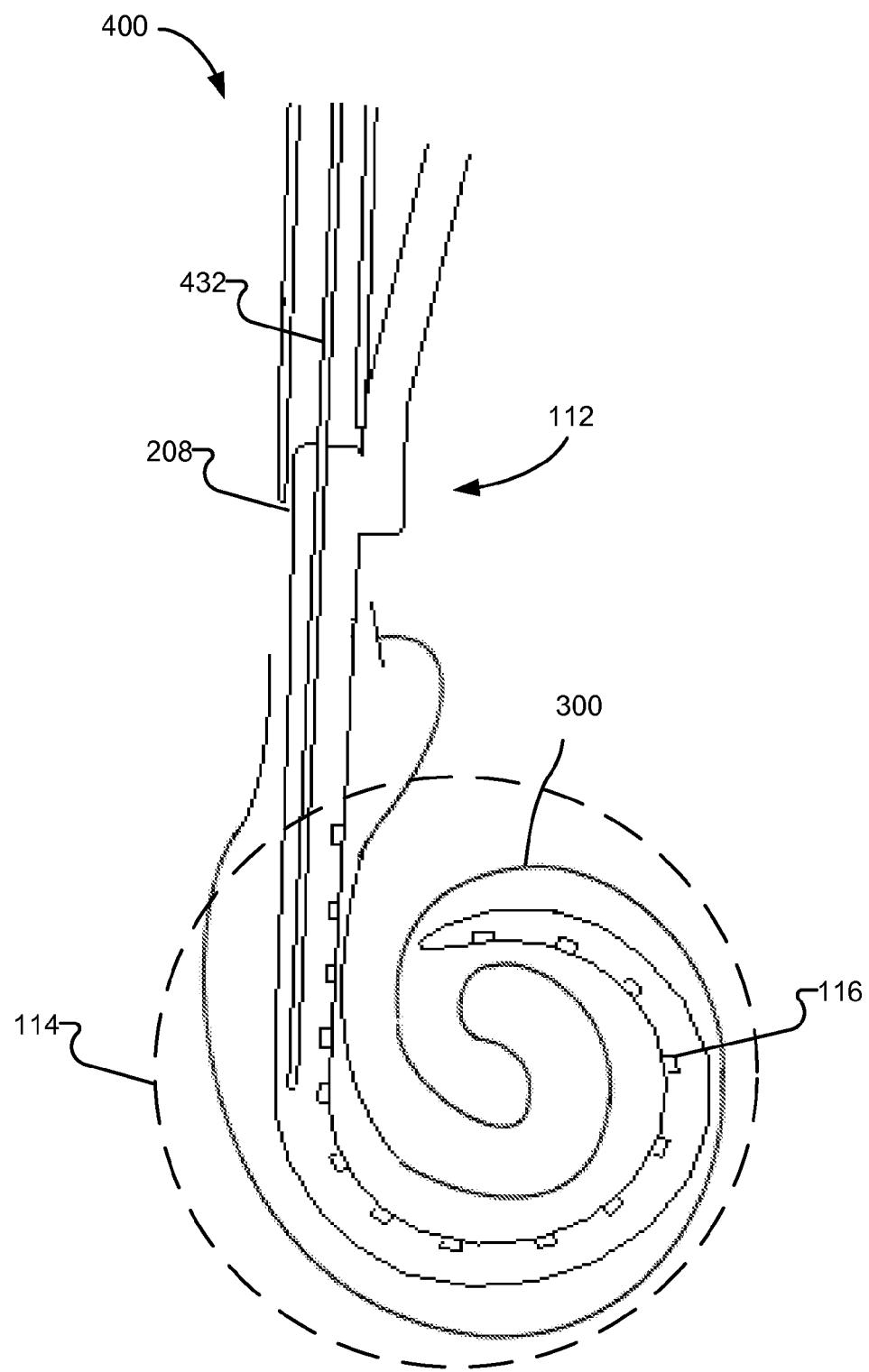
FIG. 21B shows the exemplary electrode array portion of the exemplary lead of FIG. 21A being inserted into an exemplary cochlea according to principles described herein.

Returning to FIG. 20, in step 2004, the electrode array portion of the lead may be guided into a bodily orifice with the insertion tool. For example, FIG. 21B shows electrode array portion 114 of lead 112 being guided into cochlea 300 with insertion tool 400. As shown, stiffening member 432 may be inserted at least partially into lead 112. In some examples, stiffening member 432 may provide stability and/or stiffness to lead 112 as electrode array portion 114 is guided into cochlea 300. Additionally or alternatively, electrode array portion 114 may conform to the geometry of cochlea 300 thereby positioning electrodes 116 of electrode array portion 114 such that they face the auditory nerve tissue of cochlea 300.

Figure 21D:
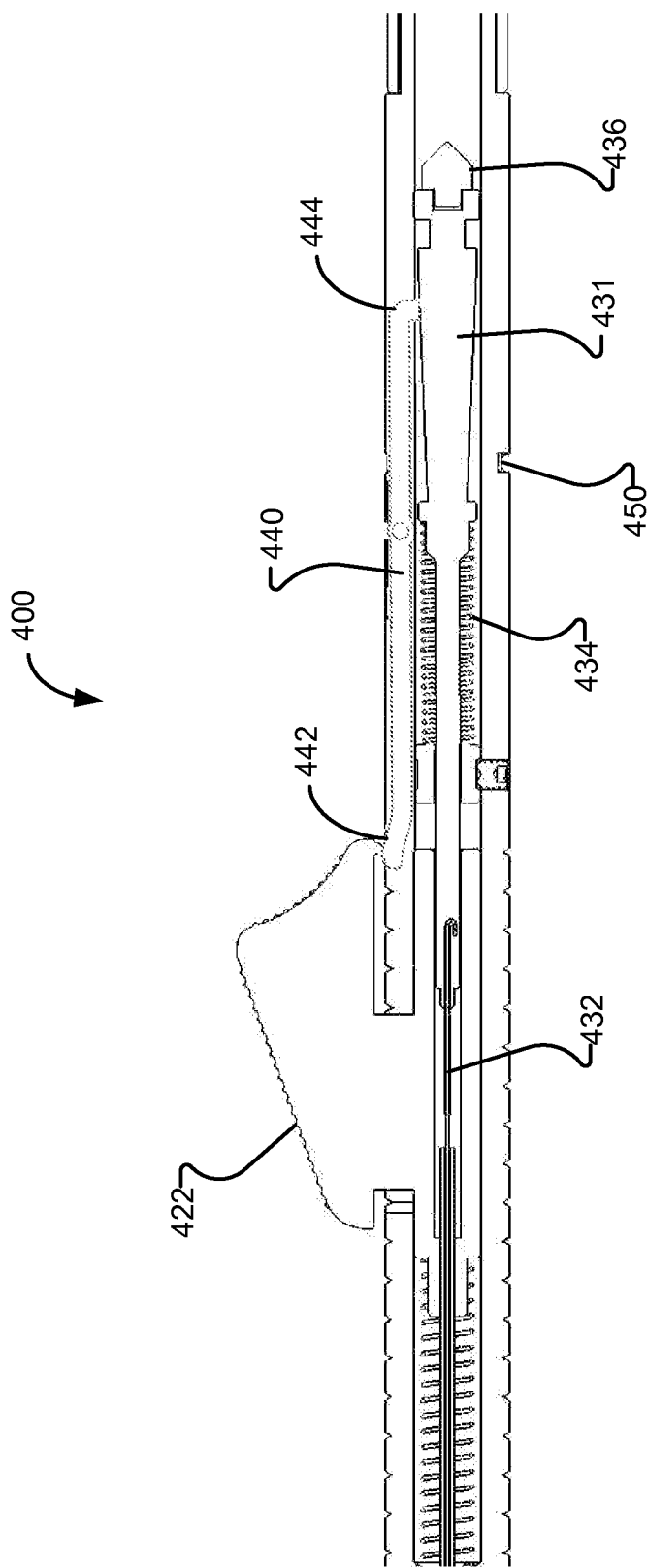
FIG. 21D shows a cross-sectional side view of the exemplary retractor assembly of the exemplary insertion tool of FIG. 21A moving in a proximal direction according to principles described herein.

Returning to FIG. 20, in step 2006, a slider member of the insertion tool may be moved from a first position to a second position to facilitate actuation of a rocker lever of the insertion tool to at least partially retract a stiffening member from the electrode array portion. For example, FIG. 21C shows insertion tool 400 with slider member 422 in the first position. To move slider member 422 from the first position to the second position, a user may advance slider member 422 in the direction indicated by arrow 2102. As a result, slider member 422 may advance to the second position, as shown in FIG. 21D. In some examples, slider member 422 may engage distal portion 442 of rocker lever 440 to actuate (e.g., pivot) rocker lever 440 as slider member 422 moves from the first position to the second position. In additional or alternative examples, moving slider member 422 from the first position to the second position may allow a user to actuate rocker lever 440 directly (e.g., with a thumb or forefinger).

Figure 21E:
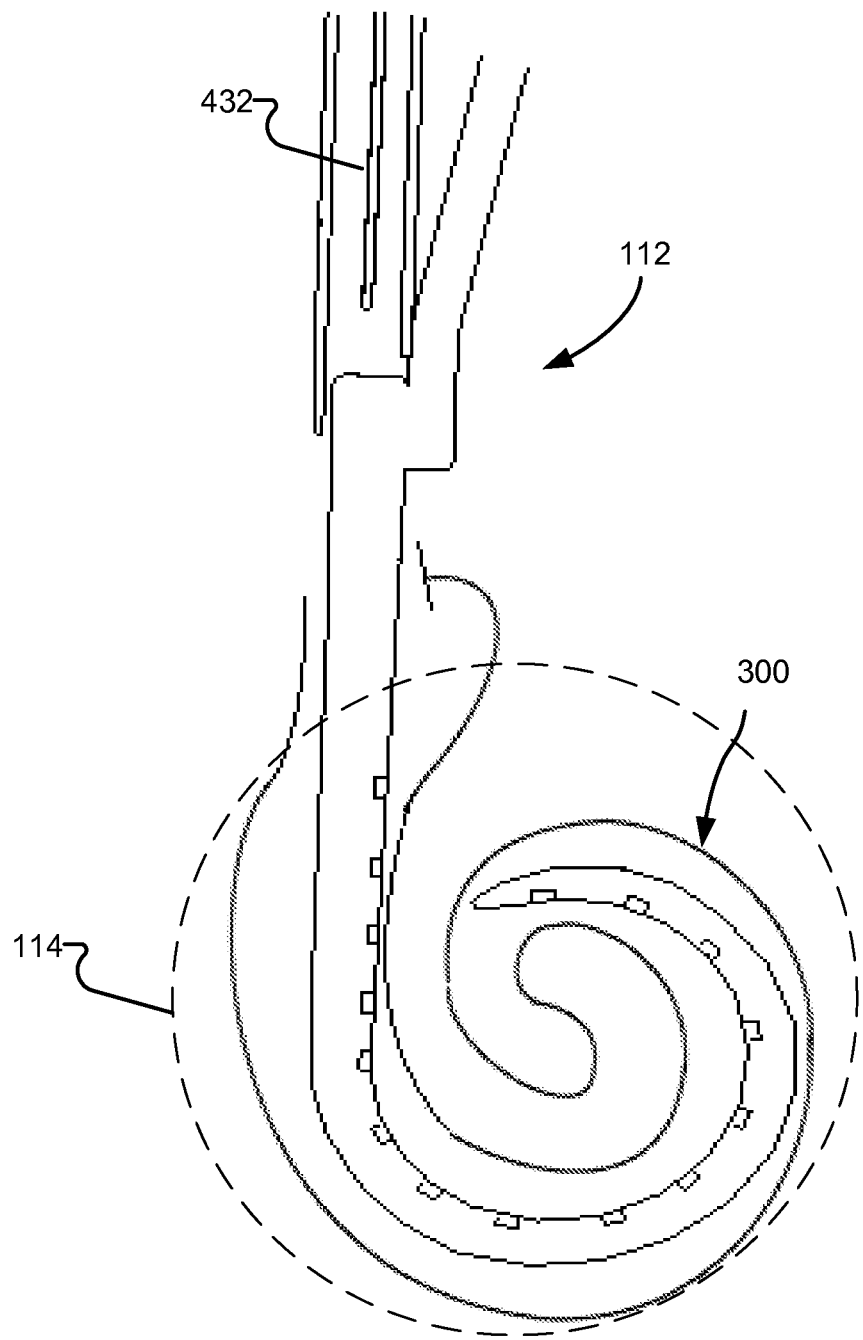
FIG. 21E shows an exemplary stiffening member of the exemplary insertion tool of FIG. 21A being retracted from the exemplary electrode array portion according to principles described herein.

Actuation of rocker lever 440 may cause proximal portion 444 to disengage retractor member 431. As a result, spring member 434 may exert a force on retractor member 431 to move retractor member from a distal position (e.g., as shown in FIG. 21C) to a proximal position (e.g., as shown in FIG. 21D). Movement of retractor member 431 from the distal position to the proximal position may at least partially retract stiffening member 432 from electrode array portion 114 of lead 112, as shown in FIG. 21E. Once stiffening member 432 has been retracted out of electrode array portion 114, a user may withdraw insertion tool 400 away from cochlea 300, leaving electrode array portion 114 of lead 112 inserted within cochlea 300.

Figure 21F:
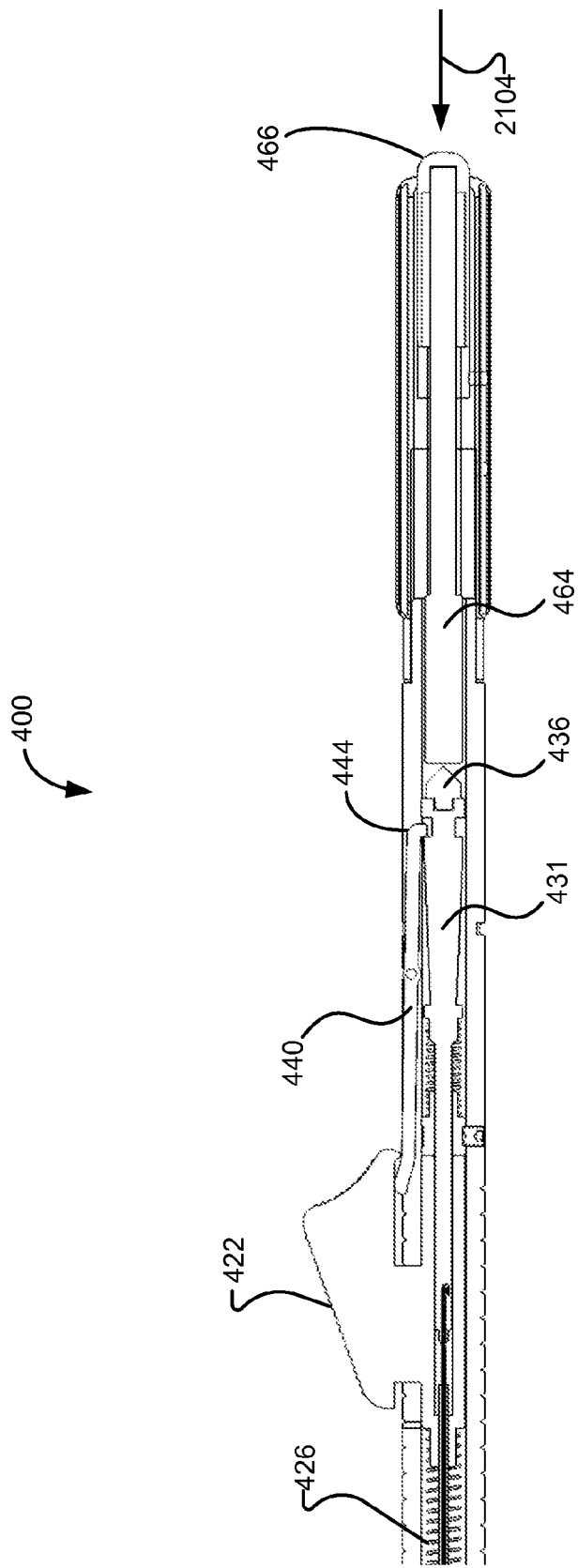
FIG. 21F shows a cross-sectional side view of the exemplary insertion tool of FIG. 21A with an exemplary plunger assembly being actuated to reset the exemplary retractor assembly, according to principles described herein.

Additionally or alternatively, the user may reset retractor member 431 from the proximal position to the distal position, as shown in FIG. 21F. As shown, to reset retractor member 431, a user may release slider member 422, which may be returned to the first position by spring member 426, and then depress button member 466 to advance plunger member 464 in a distal direction, as indicated by arrow 2104. As a result, plunger member 464 may engage shock absorber 436 to advance retractor member 431 from the proximal position to the distal position. Once in the distal position, proximal portion 444 of rocker lever 440 may engage retractor member 431 to retain retractor member 431 in the distal position, thereby allowing insertion tool 400 to be re-used to insert another electrode array portion of another lead into another bodily orifice.

The insertion tools described herein may be configured to facilitate single-handed insertion of a lead into a bodily orifice. For example, a user may grasp handle portion 411 of insertion tool 400 with a single hand and guide electrode array portion 114 into the cochlear duct. Once electrode array portion 114 has been suitably positioned, the user may retract stiffening member 432 from electrode array portion 114 utilizing insertion tool 400 by actuating slider member 422. This may be performed without substantially repositioning insertion tool 400 within the user's hand. In this manner, insertion tool 400 may provide a stable platform for the insertion of electrode array portion 114 and minimize trauma to the cochlea that may occur during the insertion procedure.

In some examples, insertion tools described herein and/or any components thereof may be disposable. For example, insertion tool 400 and/or insertion tool 1200 may be used during a single electrode array portion insertion procedure (or during two electrode array portion insertion procedures for a bilateral cochlear implant patient) and then disposed of. In this manner, insertion tool 400 and/or insertion tool 1200 does not need to be sterilized after use. Alternatively, insertion tool 400 and/or insertion tool 1200 may be sterilized after use so that it may be used in one or more subsequent insertion procedures.

Insertion tools 400 and 1200 are provided for exemplary purposes only and are not limiting. Additional insertion tools according to principles described herein may include additional or alternative elements and/or may exclude certain illustrated elements according to principles described herein.

The preceding description has been presented only to illustrate and describe embodiments of the invention. It is not intended to be exhaustive or to limit the invention to any precise form disclosed. Many modifications and variations are possible in light of the above teaching.

What is claimed is:

1. An insertion tool that facilitates insertion of an electrode array portion of a lead into a bodily orifice, the insertion tool comprising:
    a handle assembly that facilitates handling of the insertion tool;
    a slider assembly disposed at least partially within the handle assembly and that comprises
        a slider member configured to be actuated by a user to operate the insertion tool, and
        a tubular member coupled to a distal end of the slider member and configured to at least partially contain a stiffening member configured to be inserted into the electrode array portion, wherein the tubular member advances in a distal direction relative to the handle assembly in response to an advancement by the user of the slider member in the distal direction relative to the handle assembly;
    a reactor assembly disposed at least partially within the handle assembly and comprising the stiffening member and a spring-loaded reactor member couple at a distal end to the stiffening member, wherein, while the stiffening member is inserted into the electrode array portion, the spring-loaded reactor member moves from a distal position to a proximal position relative to the handle assembly to at least partially retract the stiffening member from the electrode array portion; and
    a rocker lever that
        pivots about an axle,
        selectively retains the spring-loaded retractor member in the distal position, and
        releases the spring-loaded retractor member to move from the distal position to the proximal position by pivoting about the axle in response to the advancement by the user of the slider member in the distal direction relative to the handle assembly.

2. The insertion tool of claim 1, wherein the slider member is slidable relative to the handle assembly between a first position and a second position in response to actuation of the slider member by the user.

3. The insertion tool of claim 2, wherein the slider assembly further comprises a spring member configured to return the slider member from the second position to the first position upon release of the slider member by the user.

4. The insertion tool of claim 2, wherein the slider member is configured to engage and pivot the rocker lever about the axle to release the spring-loaded retractor member to move from the distal position to the proximal position as the slider member moves from the first position to the second position.

5. The insertion tool of claim 2, wherein the slider member is configured to prevent inadvertent pivoting of the rocker lever about the axle when the slider member is in the first position and to allow pivoting of the rocker lever by the user about the axle when the slider member is in the second position.

6. The insertion tool of claim 5, wherein the slider member is configured to at least partially cover a distal portion of the rocker lever when the slider member is in the first position and to at least partially expose the distal portion of the rocker lever when the slider member is in the second position.

7. The insertion tool of claim 1, wherein the handle assembly comprises a handle portion configured to at least partially contain the retractor assembly and the slider assembly, a guide tube coupled to a distal end of the handle portion, and a holder member coupled to a distal end of the guide tube and configured to removably couple to the lead.

8. The insertion tool of claim 7, wherein the holder member comprises a slot in a distal end of the holder member, the slot configured to hold a portion of the lead.

9. The insertion tool of claim 7, wherein the holder member is configured to be rotatable relative to the guide tube to facilitate selective insertion of the electrode array portion in a right cochlea or a left cochlea.

10. The insertion tool of claim 1, further comprising a plunger assembly configured to reset the spring-loaded retractor member from the proximal position to the distal position, wherein the plunger assembly comprises:
    a plunger housing coupled to a proximal end of the handle portion and defining a lumen extending through the plunger housing in communication with the lumen of the handle portion;
    a plunger member disposed at least partially within the lumen of the plunger housing and slidable relative to the plunger housing and handle portion; and
    a button member coupled to the plunger member and extending from a proximal end of the plunger housing, wherein the button member is configured to be actuated by the user to move the plunger member in a distal direction to engage the spring-loaded retractor member and return the spring-loaded retractor member from the proximal position to the distal position.

11. The insertion tool of claim 1, further comprising a radial spring configured to engage the rocker lever and exert a constant force on the rocker lever, the constant force configured to move the rocker lever into engagement with the spring-loaded retractor member to retain the spring-loaded retractor member in the distal position.

12. The insertion tool of claim 1, wherein the stiffening member is configured to insert into a lumen that extends along a length of the electrode array portion.

13. A system comprising:
    a lead comprising an electrode array portion and configured to be coupled to an implantable cochlear stimulator; and
    an insertion tool that facilitates insertion of the electrode array portion into a bodily orifice, the insertion tool comprising
        a handle assembly that facilitates handling of the insertion took,
        a slider assembly disposed at least partially within the handle assembly and that comprises
            a slider member configured to be actuated by a user to operate the insertion tool, and
            a tubular member coupled to a distal end of the slider member and configured to at least partially contain a stiffening member configured to be inserted into the electrode array portion, wherein the tubular member advances in a distal direction relative to the handle assembly in response to an advancement by the user of the slider member in the distal direction relative to the handle assembly, a retractor assembly disposed at least partially within the handle assembly and comprising the stiffening member and a spring-loaded retractor member coupled at a distal end to the stiffening member, wherein, while the stiffening member is inserted into the electrode array portion, the spring-loaded retractor member moves from a distal position to a proximal position relative to the handle assembly to at least partially retract the stiffening member from the electrode array portion, and a rocker lever that
pivots about an axle,
selectively retains the spring-loaded retractor member in the distal position, and
releases the spring-loaded retractor member to move from the distal position to the proximal position by pivoting about the axle in response to the advancement by the user of the slider member in the distal direction relative to the handle assembly.

14. The system of claim 13, wherein the slider member is slidable relative to the handle assembly between a first position and a second position in response to actuation by the user.

15. The system of claim 14, wherein the slider member is configured to engage and pivot the rocker lever about the axle to release the spring-loaded retractor member to move from the distal position to the proximal position as the slider member moves from the first position to the second position.

16. The system of claim 14, wherein the slider member is configured to prevent inadvertent pivoting of the rocker lever about the axle when the slider member is in the first position and to allow pivoting of the rocker lever by the user about the axle when the slider member is in the second position.

17. A method of inserting an electrode array portion of a lead into a bodily orifice, the method comprising:
coupling the lead to an insertion tool, the insertion tool comprising
a handle assembly that facilitates handling of the insertion tool,
a slider assembly disposed at least partially within the handle assembly and configured to be actuated by a user to operate the insertion tool, the slider assembly comprising a slider member slidable relative to the handle assembly and a tubular member coupled to a distal end of the slider member and configured to at least partially contain a stiffening member configured to be inserted into the electrode array portion, wherein the tubular member advances in a distal direction relative to the handle assembly in response to an advancement by the user of the slider member in the distal direction relative to the handle assembly, a retractor assembly disposed at least partially within the handle assembly and comprising the stiffening member and a spring-loaded retractor member coupled at a distal end to the stiffening member, wherein, while the stiffening member is inserted into the electrode array portion, the spring-loaded retractor member moves from a distal position to a proximal position relative to the handle assembly to at least partially retract the stiffening member from the electrode array portion, and a rocker lever configured to
pivots about an axle,
selectively retains the spring-loaded retractor member in the distal position, and
releases the spring-loaded retractor member to move from the distal position to the proximal position by pivoting about the axle in response to the advancement by the user of the slider member in the distal direction relative to the handle assembly;

guiding the electrode array portion into a bodily orifice with the insertion tool; and moving the slider member from a first position to a second position relative to the handle assembly to facilitate pivoting of the rocker lever about the axle to release the spring-loaded retractor member to move from the distal position to the proximal position to at least partially retract the stiffening member from the electrode array portion.

18. The method of claim 17, wherein as the slider member moves from the first position to the second position, the slider member engages and pivots the rocker lever about the axle to release the spring-loaded retractor member.

19. The method of claim 17, wherein as the slider member moves from the first position to the second position, the slider member at least partially exposes the rocker lever to allow pivoting of the rocker lever about the axle by the user.

* * * * *